US010231626B2

(12) United States Patent
Steinbach et al.

(10) Patent No.: US 10,231,626 B2
(45) Date of Patent: Mar. 19, 2019

(54) IMAGING SYSTEM AND METHOD FOR FLUORESCENCE GUIDED SURGERY

(71) Applicant: The Regents of the University of California, Oakland, CA (US)

(72) Inventors: Paul Steinbach, San Diego, CA (US); Quyen T. Nguyen, La Jolla, CA (US); Roger Y. Tsien, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 434 days.

(21) Appl. No.: 14/216,704

(22) Filed: Mar. 17, 2014

(65) Prior Publication Data

US 2014/0276008 A1    Sep. 18, 2014

Related U.S. Application Data

(60) Provisional application No. 61/799,381, filed on Mar. 15, 2013.

(51) Int. Cl.
*A61B 5/00* (2006.01)

(52) U.S. Cl.
CPC .......... *A61B 5/0071* (2013.01); *A61B 5/0059* (2013.01); *A61B 5/0062* (2013.01); *A61B 5/0077* (2013.01)

(58) Field of Classification Search
CPC . A61B 1/00009; A61B 1/00186; A61B 1/043; A61B 1/0638; A61B 1/0646; A61B 1/00045; A61B 1/0005; A61B 1/00096; A61B 1/00172; A61B 1/07; A61B 5/0071; A61B 5/0059; A61B 5/0086; A61B 5/742; A61B 5/0077; A61B 2017/00057; A61B 90/36; A61B 90/30; A61B 90/361; A61B 18/20; A61B 2018/00904;
(Continued)

(56) References Cited

U.S. PATENT DOCUMENTS 5,677,762 A * 10/1997 Ortyn ................... G02B 21/082 356/39
2006/0114553 A1* 6/2006 Laudo ...................... B01L 9/06 359/368

(Continued)

OTHER PUBLICATIONS

Blum, G. et al., "Comparative Assessment of Substrates and Activity Based Probes as Tools for Non-Invasive Optical Imaging of Cysteine Protease Activity," PLoS ONE, Jul. 2009, vol. 4, No. 7, pp. 1-10.

(Continued)

*Primary Examiner* — Carolyn Pehlke
(74) *Attorney, Agent, or Firm* — Morgan Lewis & Bockius LLP

(57) ABSTRACT

Imaging systems for fluorescence guided surgery are provided. An imaging system comprises a light source unit for providing one or more illumination and excitation lights to a target, a detection unit for detecting reflectance and fluorescence from the target, an optical train for directing the one or more illumination and excitation lights from the light source unit to the target and for directing the reflectance and fluorescence from the target to the detection unit, and a control unit for controlling the light source unit and the detection unit. Imaging methods for fluorescence guided surgery are also provided.

13 Claims, 12 Drawing Sheets

(58) Field of Classification Search
CPC ........ A61B 2090/306; A61B 2090/309; A61B 2090/371; A61B 2090/373; A61B 2034/2055; A61B 34/20; A61B 3/0008; G02B 21/0028; G02B 21/0032; G02B 21/0064; G02B 21/082; G02B 21/18; G02B 21/365; G02B 23/2484; G06T 5/009; G06T 5/40
USPC ....... 600/476, 473, 160, 178, 424, 427, 478, 600/109, 118, 181, 249, 407, 477, 479; 348/223.1, 68, E09.052, E7.087, E9.052, 348/143, 65, 77
See application file for complete search history.

(56) References Cited

U.S. PATENT DOCUMENTS

| | | | |
|---|---|---|---|
| 2009/0146077 A1* | 6/2009 | Moy | A61B 1/0638 250/458.1 |
| 2012/0212619 A1* | 8/2012 | Nagamune | H04N 5/2256 348/164 |
| 2013/0041267 A1* | 2/2013 | Ntziachristos | A61B 1/00009 600/476 |

OTHER PUBLICATIONS

Blum, G. et al., "Dynamic imaging of protease activity with fluorescently quenched activity-based probes," *Nature Chemical Biology*, Sep. 2005, vol. 1, No. 4, pp. 203-209.
Blum, G. et al., "Noninvasive optical imaging of cysteine protease activity using fluorescently quenched activity-based probes," *Nature Chemical Biology*, Oct. 2007, vol. 3, No. 10, pp. 668-677.
De Grand, A.M. et al., "An Operational Near-Infrared Fluorescence Imaging System Prototype for Large Animal Surgey," *Technology in Cancer Research & Treatment*, Dec. 2003, vol. 2, No. 6, pp. 553-562.
Figueiredo, J-L. et al., "Near infrared thorascoscopy of tumoral protease activity for improved detection of peripheral lung cancer," *Int. J. Cancer*, 2006, vol. 118, pp. 2672-2677.
Gioux, S. et al., "Image-Guided Surgery Using Invisible Near-Infrared Light: Fundamentals of Clinical Translation," *Molecular Imaging*, Sep.-Oct. 2010, vol. 9, No. 5, pp. 237-255.
Gray, D.C. et al., "Dual-mode laparoscopic fluorescence image-guided surgery using a single camera," *Biomedical Optics Express*, Aug. 1, 2012, vol. 3, No. 8, pp. 1880-1890.
Jiang, T. et al., "Tumor imaging by means of proteolytic activation of cell-penetrating peptides," PNAS, Dec. 21, 2004, vol. 101, No. 51, pp. 17867-17872.
Kashiwagi, M. et al., "Feasibility of Noninvasive Assessment of Thin-Cap Fibroatheroma by Multidetector Computed Tomography," *JACC: Cardiovascular Imaging*, 2009, vol. 2, No. 12, pp. 1412-1419.
Keereweer, S. et al., "Optical Image-guided Surgery-Where Do We Stand?" *Mol Imaging Biol*, 2011, vol. 13, pp. 199-207.
Liu, Y. et al., "Hands-free, wireless goggles for near-infrared fluorescence and real-time image-guided surgery," *Surgery*, 2011, vol. 149, pp. 689-698.
Mendizabal Ruiz, E.G. et al., "Analysis of Contrast-Enhanced Intravascular Ultrasound Images for the Assessment of Coronary Plaque Neoangiogenesis: Another Step Closer to the Identification of the Vulnerable Plaque," *Current Pharmaceutical Design*, 2012, vol. 18, pp. 2207-2213.
Nguyen, Q.T. et al., "Fluorescence-guided surgery with live molecular navigation—a new cutting edge," *Nature Reviews Cancer*, Sep. 2013, vol. 13, pp. 653-662.
Nguyen, Q.T. et al., "Surgery with molecular fluorescence imaging using activatable cell-penetrating peptides decreases residual cancer and improves survival," PNAS, Mar. 2, 2010, vol. 107, No. 9, pp. 4317-4322.

Olson, E.S. et al., "Activatable cell penetrating peptides linked to nanoparticles as dual probes for in vivo fluorescence and MR imaging of proteases," PNAS, Mar. 2, 2010, vol. 107, No. 9, pp. 4311-4316.
Olson, E.S. et al., "In vivo characterization of activatable cell penetrating peptides for targeting protease activity in cancer," *Integr. Biol.*, 2009, vol. 1, pp. 382-393.
Olson, E.S. et al., "In vivo fluorescence imaging of atherosclerotic plaques with activatable cell-penetrating peptides targeting thrombin activity," *Integr Biol (Camb).*, Jun. 2012, vol. 4, No. 6, pp. 595-605.
Orosco, R.K. et al., "Fluorescence Imaging in Surgery," *IEEE Reviews in Biomedical Engineering*, 2013, vol. 6, pp. 178-187.
Partovi, S. et al., "Contrast-Enhanced Ultrasound for Assessing Carotid Atherosclerotic Plaque Lesions," *AJR*, Jan. 2012, vol. 198, pp. W13-W19.
Piccirillo, SGM. et al., "Fluorescence-guided surgical sampling of glioblastoma identifies phenotypically distinct tumour-initiating cell populations in the tumor mass and margin," *British Journal of Cancer*, 2012, vol. 107, pp. 462-468.
Pierce, M.C. et al., "Optical contrast agents and imaging systems for detection and diagnosis of cancer," *Int. J. Cancer*, 2008, vol. 123, pp. 1979-1990.
Roessler, K. et al., "Intraoperative tissue fluorescence using 5-aminolevolinic acid (5-ALA) is more sensitive than contrast MRI or amino acid positron emission tomography ($^{18}$F-FET PET) in glioblastoma surgery," *Neurological Research*, 2012, vol. 34, No. 3, pp. 314-317.
Savariar, E.N. et al., "Real-time In Vivo Molecular Detection of Primary Tumors and Metastases with Ratiometric Activatable Cell-Penetrating Peptides," *Cancer Res*, 20012, vol. 73, No. 2, pp. 855-864.
Sheth, R.A. et al., "Improved detection of ovarian cancer metastases by introperative quantitative fluorescence protease imaging in a pre-clinical model," *Gynecologic Oncology*, 2009, vol. 112, pp. 616-622.
Stummer, W. et al., "Fluorescence-guided resection of glioblastoma multiforme by using 5-aminolevulinic acid-induced porphyrins: a prospective study in 52 consecutive patients," *J Neurosurg*, 2000, vol. 93, pp. 1003-1013.
Stummer, W. et al., "Fluorescence-guided surgery with 5-aminolevulinic acid for resection of malignant glioma: a randomised controlled multicentre phase III trial," *Lancet Oncol*, 2006, vol. 7, pp. 392-401.
Taruttis, A. et al., "Translation Optical Imaging," *AJR*, Aug. 2012, vol. 199, pp. 263-271.
Themelis, G. et al., "Multispectral imaging using multiple-bandpass filters," *Optics Letters*, May 1, 2008, vol. 33, No. 9, pp. 1023-1025.
Themelis, G. et al., "Real-time intraoperative fluorescence imaging system using light-absorption correction," *Journal of Biomedical Optics*, Nov./Dec. 2009, vol. 14, No. 6, pp. 064012-1-064012-9.
Tran Cao, H.S. et al., "Tumor-Specific Fluorescent Antibody Imaging Enable Accurate Staging Laparoscopy in an Orthotopic Model of Pancreatic Cancer," *Hepatogastroenterology*, Sep. 2012, vol. 59, No. 118, pp. 1994-1999.
Troyan, S.L. et al., "The FLARE™ Intraoperative Near-Infrared Fluorescence Imaging System: A First-in-Human Clinical Trial in Breast Cancer Sentinel Lymph Node Mapping," *Ann Surg Oncol*, 2009, vol. 16, pp. 2943-2952.
Van Dam, G.M. et al., "Intraoperative tumor-specific fluorescence imaging in ovarian cancer by folate receptor-α targeting: first in-human results," *Nature Medicine*, Oct. 2011, vol. 17, No. 10, pp. 1315-1319.
Verbeck, F.P.R. et al., "Image-guided hepatopancreatobiliary surgery using near-infrared fluorescent light," *J Hepatobiliary Pancreat Sci*, 2012, vol. 19, pp. 626-637.
Whitney, M. et al., "Ratiometric Activatable Cell-Penetrating Peptides Provide Rapid In Vivo Readout of Thrombin Activation," *Angew. Chem. Int. Ed.*, 2013, vol. 52, pp. 325-330.
Whitney, M.A. et al., "Fluorescent peptides highlight peripheral nerves during surgery in mice," *Nature Biotechnology*, Apr. 2011, vol. 29, No. 4, pp. 352-356.

(56) References Cited

OTHER PUBLICATIONS

Wu, A.P. et al., "Improved Facial Nerve Identification with Novel Fluorescently Labeled Probe," *The Laryngoscope*, Apr. 2011, vol. 121, pp. 805-810.

* cited by examiner

A          B          C

IMAGING SYSTEM AND METHOD FOR FLUORESCENCE GUIDED SURGERY

CROSS REFERENCE TO RELATED APPLICATIONS

The present application claims priority to U.S. Provisional Application No. 61/799,381, filed on Mar. 15, 2013, and which is incorporated herein by reference in its entirety for all purposes.

STATEMENT AS TO RIGHTS TO INVENTIONS MADE UNDER FEDERALLY-SPONSORED RESEARCH OR DEVELOPMENT

This invention was made with Government support under CA158448, EB008122, and EB014929 awarded by the National Institutes of Health and W81XWH-05-1-0183, W81XWH-09-1-0699 awarded by the Army. The Government has certain rights in this invention.

FIELD OF THE DISCLOSURE

The disclosed embodiments are generally related to imaging systems and the methods for fluorescence guided surgery.

BACKGROUND OF THE INVENTION

It is not practical to conduct surgery while viewing only the fluorescence of a contrast agent. Instead, fluorescence images need to be superimposed continuously in real-time and in precise spatial register with reflectance images showing the morphology of the normal tissue and the location of the surgical instruments. Reflectance is inherently brighter than fluorescence, in that the fraction of incident photons returned by reflectance is much higher than that from fluorescence (even from strongly labeled tissue). Also, fluorescence requires spectral separation between bright short-wavelength excitation and relatively dim longer-wavelength emission, filtered to remove reflected excitation wavelengths.

The simplest approach to overlaying a reflectance image with a fluorescent one does not require a camera at all—the image is simply viewed by the eye. This approach is feasible primarily for dyes excited in the violet or blue, with excitation and emission filters tailored to provide a mixture of reflectance and fluorescence directly visible by the surgeon. An early example was the visualization of the fluorescence from protoporphyrin IX (Leica FL400-excitation at 380-420 nm, display at 480-720 nm and Zeiss OPMI Pentero—excitation 400-410 nm, display 620-710 nm) generated in tumors by systemic administration of the metabolic precursor, 5-aminolevulinic acid (Stummer, W. et al. Fluorescence-guided surgery with 5-aminolevulinic acid for resection of malignant glioma: a randomised controlled multicentre phase III trial. The lancet oncology 7: 392-401 (2006)). In both these examples, the red emission filter was deliberately designed to leak at shorter wavelengths so that normal tissue landmarks and surgical instruments were visible by the violet reflectance light while the cancer tissue glowed red. Normal full color reflectance was sacrificed so that image processing could be completely avoided. Similarly, fluorescein fluorescence (Zeiss Pentero—excitation 488 nm, emission >500 nm) was viewed with an excitation filter mainly passing blue but with some leakage of green and red, paired with an emission filter preferentially passing green but with slight leakage of blue and somewhat more of red. The leakages allow blue, green, and red reflectances to generate a reasonable white-light reflectance image with green fluorescence superimposed. The advantage of these approaches is that the only modification of standard equipment is the inclusion of judiciously tailored excitation and emission filters. The disadvantages are 1) inflexibility, in that the filters have to be optimized for a given tissue concentration of a given dye, 2) spectral distortion of the reflectance image (in the worst case, confinement to violet), and 3) complete reliance on the surgeon's subjective color discrimination to decide how much fluorescence is sufficient to warrant resection.

The next level of sophistication for overlaying a reflectance image with a fluorescent one requires the use of two cameras and therefore cannot be viewed directly by eye. With this approach, two cameras collect two separate images, one for the white light reflectance image and one for the fluorescence image. Separate cameras mean that the gain for each image can be controlled independently and that the reflectance camera no longer has to look through the emission filter of the fluorescence camera. This is the obvious approach (De Grand, A. M. & Frangioni, J. V. An operational near-infrared fluorescence imaging system prototype for large animal surgery. Technology in cancer research & treatment 2: 553-62 (2003) and Troyan, S. L. et al. The FLARE intraoperative near-infrared fluorescence imaging system: a first-in-human clinical trial in breast cancer sentinel lymph node mapping. Annals of surgical oncology 16: 2943-52 (2009)) when the fluorophore excitation and emission wavelengths are in the NIR, because the surgical field can be illuminated with white visible light (400-650 nm) plus 760 nm in the case of indocyanine green. The reflectance camera sees the white light reflectance but not the NIR excitation, while the fluorescence camera sees the 800 nm emission through a suitable long-pass filter (Troyan, S. L. et al. The FLARE intraoperative near-infrared fluorescence imaging system: a first-in-human clinical trial in breast cancer sentinel lymph node mapping. Annals of surgical oncology 16: 2943-52 (2009)). A bit more ingenuity is required when the fluorophore excitation and emission are at visible wavelengths. One solution is to confine the excitation to three narrow spectral lines of blue, green, and red, say 488, 543, and 633 nm (Themelis, G., Yoo, J. S. & Ntziachristos, V. Multispectral imaging using multiple-bandpass filters. Optics letters 33: 1023-5 (2008)) whose relative intensities are adjusted to generate a reasonable simulation of white light for the reflectance camera. Ideally one of these wavelengths should be optimal for exciting the fluorophore. Meanwhile the fluorescence camera looks through an emission filter selective for one or more of the wavelength gaps between the sharp excitation lines. Depending on the fluorophore, some sacrifice of emission bandpass is likely to be necessary to avoid interference from the next longer illumination line.

Fluorescence Guided Surgery is a method of enhancing visual contrast for specific tissues and organs during surgery, providing an important tool for extending the visual differentiation between tissue targeted for excision and tissue intended for preservation beyond that which is available with white light alone. Examples of such relevant targets include tumors, nerves, and blood vessels (Orosco, R., Tsien, R. & Nguyen, Q. Fluorescence Imaging in Surgery. IEEE Reviews in Biomedical Engineering 6: 178-187 (2013) and Nguyen, Q. & Tsien, R. Fluorescence Guided Surgery with Live Molecular Navigation—A New Cutting Edge (Strategies to improve surgery). Nature Reviews Cancer 13: 653-62 (2013)).

This present disclosure and invention addresses the problem of simultaneously viewing of 1) the surgical field with white light reflectance (what all surgeons are trained to do) in conjunction with 2) fluorescently labeled targets. The present disclosure provides methods for achieving optical contrast between the fluorescently labeled target and the remainder of surgical field seen with white light reflectance by overlaying a fluorescent image of the surgical field with a live color image of the same field. The fluorescent portion of the image is pseudocolored with a hue that is not normally present in mammalian tissue; allowing the surgeon to easily distinguish between normal tissue and targeted tissue. This invention is designed to work with any fluorophore, at any excitation or emission wavelength. The invention can handle multiple individual fluorophores as well as fluorescence resonance energy transfer (FRET) fluorophore pairs, simultaneously with white light reflectance. In addition the, invention can be adapted to systems with binocular vision for improved depth of field during surgery.

SUMMARY OF THE INVENTION

In some embodiments, the present disclosure provides an imaging system for fluorescence guided surgery, comprising:
(A) a light source unit for providing one or more illumination and excitation lights to a target, the light source unit comprising a plurality of light engines, wherein
  (i) a first light engine in the plurality of light engines emits a first light for illuminating the target, and
  (ii) a second light engine in the plurality of light engines emits a second light for exciting a first fluorophore in the target;
(B) a detection unit comprising a plurality of detectors for detecting reflectance and fluorescence from the target, thereby producing a plurality of images, wherein
  (i) a first detector in the plurality of detectors detects the reflectance from the target, thereby producing a reflectance image in the plurality of images, and
  (ii) a second detector in the plurality of detectors detects a first fluorescence emitted by the excited first fluorophore, thereby producing a first fluorescence image;
(C) an optical train for directing the one or more illumination and excitation lights from the light source unit to the target and for directing the reflectance and fluorescence from the target to the detection unit; and
(D) a control unit for controlling the light source unit and the detection unit.

In some embodiments, the imaging system, further comprises a display unit for displaying an image in the plurality of images.

In some embodiments, the third light engine in the plurality of light engines emits a third light for exciting a second fluorophore in the target; and a third detector in the plurality of detectors detects a second fluorescence emitted by the excited second fluorophore, thereby producing a second fluorescence image.

In some embodiments, the light engine in the plurality of light engines comprises an array of LED chips.

In some embodiments, the first light engine in the plurality of light engines emits a white light.

In some embodiments, the light source unit is controlled by the control unit such that only one light engine in the plurality of light engines is energized at a time.

In some embodiments, the light source unit is controlled by the control unit such that each light engine in the plurality of light engines is energized sequentially.

In some embodiments, the control unit synchronizes the light source unit and the detection unit.

In some embodiments, the first detector in the plurality of detectors detects comprises a color camera.

In some embodiments, the second detector in the plurality of detectors detects comprises a first monochrome camera.

In some embodiments, the third detector in the plurality of detectors detects comprises a second monochrome camera.

In some embodiments, the optical train comprises a light pipe homogenizer in a light illumination path for producing a uniform distribution of an excitation light across the target.

In some embodiments, the optical train comprises one or more mirrors in a light detection path for splitting lights between or among the plurality of detectors.

In some embodiments, the second light is collimated and filtered before being directed to the target, using a first narrow-band interference filter.

In some embodiments, each of the second light and the third light the second light is collimated and filtered before being directed to the target.

In some embodiments, the control unit and the display unit are embedded in a computer.

In some embodiments, the display unit displays the plurality of images by overlying the reflectance image with one or more fluorescence images in real-time.

In some embodiments, an image processing method for fluorescence guided surgery, comprising:
  at a computer system having one or more processors and memory storing one or more programs executed by the one or more processors:
    (A) acquiring a plurality of images using a detection unit, wherein the plurality of images comprises a reflectance image and one or more fluorescence images;
    (B) determining one or more transparency factors, wherein each respective transparency factor in the one or more transparency factors is a ratio of a fluorescence intensity of a corresponding fluorescence image in the one or more fluorescence images divided by a maximum allowed fluorescence intensity of the corresponding fluorescence image in the one or more fluorescence images;
    (C) factoring RGB coordinates of each image in the plurality of images, thereby producing a plurality of factored RGB coordinates, wherein
      (i) a factored RGB coordinate in the plurality of factored RGB coordinates is the product of a RGB coordinate of the fluorescence image times a corresponding transparency factor of the corresponding fluorescence image, and
      (ii) a factored RGB coordinate for a reflectance image is the product of a RGB coordinate of the reflectance image times a predetermined constant minus a sum of the one or more transparency factors, wherein the sum of the one or more transparency factors does not exceed the predetermined constant; and
    (D) generating a display image by establishing a display RGB coordinate based on the plurality of factored RGB coordinates, wherein the display RGB coordinate equals to a sum of the plurality of factored RGB coordinates.

In some embodiments, the one or more fluorescence images comprises a first fluorescence image.

In some embodiments, the one or more fluorescence images comprises a first fluorescence image and a second fluorescence image.

In some embodiments, the one or more fluorescence images comprises more than two fluorescence images.

In some embodiments, the RGB coordinate of a fluorescence image or a factored fluorescence image is a brightness coordinate for a given overlay color.

In some embodiments, the image processing method further comprises:

displaying the display image in a display unit.

In some embodiments, the image processing method for fluorescence guided surgery comprises:

at a computer system having one or more processors and memory storing one or more programs executed by the one or more processors:
(A) acquiring a plurality of images using a detection unit, wherein the plurality of images comprises two fluorescence images;
(B) generating a ratio image, wherein a ratio pixel coordinate of the ratio image is determined based on a hue value and a brightness value, wherein
   (i) the hue value is determined based on a ratio of the two fluorescence images, and
   (ii) the brightness value is determined based on an intensity of one of the two fluorescence images; and
(C) generating a display image by establishing a display RGB coordinate, wherein the display RGB coordinate is determined by using a lookup table with the hue value and the brightness as inputs.

In some embodiments, the plurality of images comprises a black and white reflectance image and the method further comprises:
(D) determining a transparency factor prior to the generating the display image, wherein the transparency factor is a ratio of a fluorescence intensity of one of the two fluorescence images divided by a maximum allowed fluorescence intensity of the corresponding fluorescence image of the two fluorescence images; and
(E) factoring RGB coordinates of the reflectance image and the ratio image, subsequent to the generating the ratio image, producing a plurality of factored RGB coordinates, wherein
   (i) a factored RGB coordinate for the ratio image is the product of a RGB coordinate of the ratio image times the transparency factor, and
   (ii) a factored RGB coordinate for the reflectance image is the product of a RGB coordinate of the reflectance image times a predetermined constant minus the transparency factor, wherein the transparency factor does not exceed the predetermined constant,
wherein the display RGB coordinate equals to a sum of the plurality of factored RGB coordinates.

In some embodiments, the plurality of images comprises a black and white reflectance image and the method further comprises:
(D) determining a transparency factor prior to the generating the display image, wherein the transparency factor is a ratio of a fluorescence intensity of one of the two fluorescence images divided by a maximum allowed fluorescence intensity of the corresponding fluorescence image of the two fluorescence images;
(E) determining a gamma factor; and
(F) factoring RGB coordinates of the reflectance image and the ratio image, subsequent to the generating the ratio image, producing a plurality of factored RGB coordinates, wherein
   (i) a factored RGB coordinate for the ratio image is the product of a RGB coordinate of the ratio image times the transparency factor to the power of the gamma factor, and
   (ii) a factored RGB coordinate for the reflectance image is the product of a RGB coordinate of the reflectance image times a predetermined constant minus the transparency factor to the power of the gamma factor, wherein the transparency factor to the power of the gamma factor does not exceed the predetermined constant,
wherein the display RGB coordinate equals to a sum of the plurality of factored RGB coordinates.

In some embodiments, the ratio of the two fluorescence images is encoded as a spectrum of colors.

In some embodiments, the spectrum of colors is from blue to red.

In some embodiments, the spectrum of colors is from blue to red, with blue corresponding to low ratio values and red corresponding to high ratio values.

In some embodiments, the predetermined constant is one.

BRIEF DESCRIPTION OF THE DRAWINGS

The accompanying drawings, which are incorporated into and constitute a part of this specification, illustrate one or more embodiments of the present application and, together with the detailed description, serve to explain the principles and implementations of the application.

DETAILED DESCRIPTION OF THE INVENTION

1) The present disclosure provides a method for alternating color and fluorescent images in the surgical field with no inherent restriction on the number or type of targeted fluorophores. The present disclosure provides methods for alternating color and fluorescent images in the surgical field with no compromise on the optical pathway used to generate the fluorescent images. The present disclosure contemplates the use of any stable, high-speed light source for illumination of the target, including but not limited to LED, lasers, and xenon flash lamps 2) The present disclosure provides method for producing uniform distribution of light at surgical field. 3) The present disclosure provides method for reducing specular reflectance in white light image.

This present disclosure provides methods for simultaneous, intraoperative visualization of different molecularly targeted fluorescent markers with no restriction on the number or type of targeted fluorophores, and this capability extends the visual repertoire of the operating surgeon beyond white light reflectance, improving detection of tumor margin and critical structures (i.e., nerves, vasculature). Currently, there are two fluorescent agents that are FDA approved for clinical use (ICG and fluorescein) but many more are in development.

This present disclosure also provides methods for minimizes distracting specular reflection from wet surfaces in the reflected white light image for whole mouse imaging. To our knowledge, this technology has not been implemented in any human, mouse or gel imagers in the commercial marketplace.

This present disclosure provides methods for homogenizing the distribution of excitation light at the specimen plane for whole mouse imaging. This light pipe technology is borrowed from the commercial video projectors market. This technology has not been applied to any human, mouse imagers, gel readers, or light microscope in the biological marketplace.

Imaging Systems

Figure 2A:
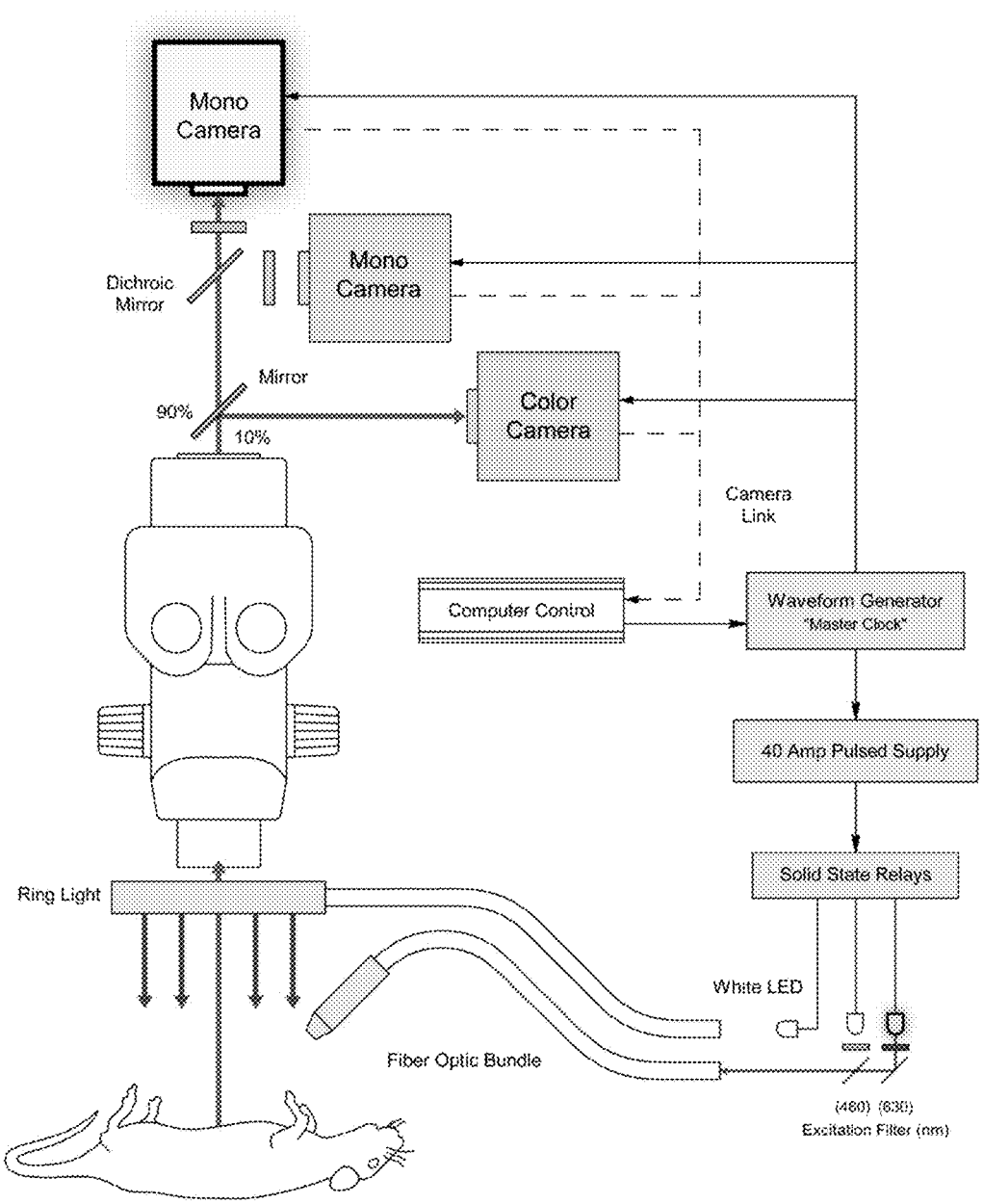
FIGS. 2A-2B provide for graphical representations of exemplary imaging systems, in accordance with some embodiments of the present disclosure. System Diagram showing the major components of the system with each of the LED light system sequentially active, white light LED followed by the two fluorescent channels.
Figure 2B:
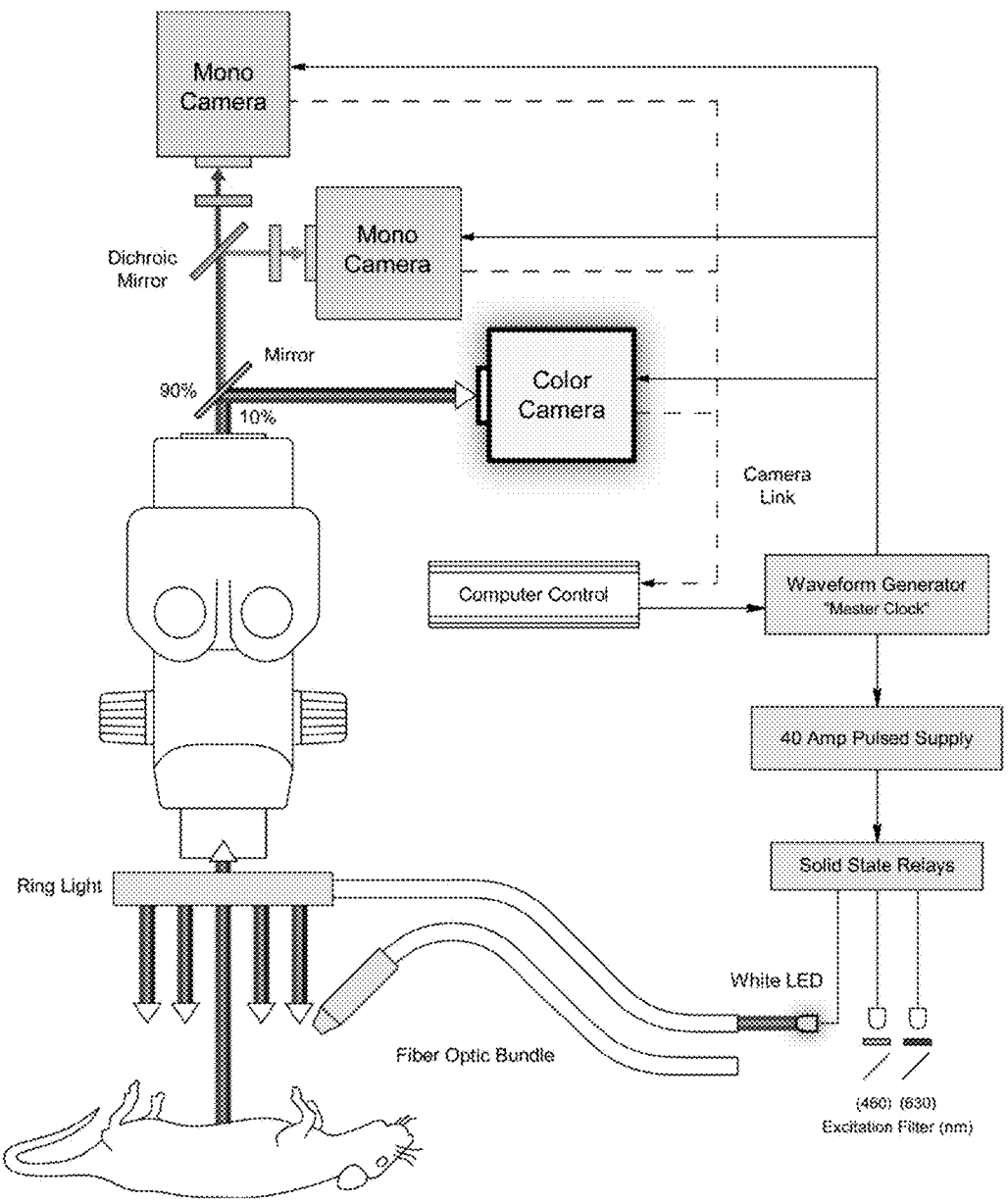

According to the present disclosure, imaging systems are provided. In some embodiments, the imaging systems consist of four major components, light source, lens, cameras and computer or other system controller (see, for example, FIG. 2). In some embodiments, other than the computer or other system controller, these components have been optimized to address the needs for small animal surgeries, including microscale surgeries on a variety of animals, including mice and humans.

In some embodiments, the imaging system consists of one, two or three real-time, high-resolution cameras, a color camera. In some embodiments, the imaging system consists of one real-time, high-resolution camera, one color camera. In some embodiments, the imaging system consists of one or two real-time, high-resolution cameras, one color camera and one monochrome camera. In some embodiments, the imaging system consists of one, two or three real-time, high-resolution cameras, a color camera and two monochrome cameras. In some embodiments, the cameras are super-resolution cameras.

In some embodiments, while the three cameras see exactly the same field of view, they capture different information. The color camera captures a high-resolution, full color image of the field of view—a view that is familiar to surgeons—while the monochrome cameras capture a fluorescent emission image of the same field. The key to capturing these three different images, is the use of a high-speed pulsed light source that is synchronized with the image capturing process. Whenever the color camera captures an image, a broadband white light source illuminates the surgical field; likewise, whenever a given monochrome camera is active, a narrow-band light source optimized for excitation of its targeted fluorophore illuminates the field. In some embodiments, LEDs (light emitting diodes) are used for both light sources. LEDs provide fast on and off times, well defined emission spectra (using interference filters—FIG. 4) and exceptional short and long-term stability. In addition to providing a user interface, the system's computer synchronizes the cameras and LEDs, captures the live video streams, overlays the three images in host memory and displays them in real-time. No moving parts or filter wheels are required by the system since all switching is done electronically.

In some embodiments, the present disclosure provides an imaging system for fluorescence guided surgery. Such imaging systems comprise a variety of components, including (A) a light source unit for providing one or more illumination and excitation lights to a target, the light source unit comprising a plurality of light engines, (B) a detection unit comprising a plurality of detectors for detecting reflectance and fluorescence from the target, thereby producing a plurality of images, (C) an optical train for directing the one or more illumination and excitation lights from the light source unit to the target and for directing the reflectance and fluorescence from the target to the detection unit; and (D) a control unit for controlling the light source unit and the detection unit.

Optical Train

An optical train, also referred to as an optical assembly, is an arrangement of lenses employed as part of an imaging system and which functions to guide a laser. The position and angle of lenses may be adjusted to guide a laser through the path required and such adjustments would be within the level of skill of one of skill in the art to adjust as needed for an imaging system. In some embodiments, the imaging system includes an optical train for directing the one or more illumination and excitation lights from the light source unit to the target and for directing the reflectance and fluorescence from the target to the detection unit.

In some embodiments, the optical train for the instrument is based on a modified Olympus MVX10 macro-view zoom microscope. In some embodiments, the MVX10 provides front-end image collection and optical zoom with high light collection efficiency. In some embodiments, the imaging system includes a color camera and two monochrome cameras. In some embodiments, at the image forming end of the optical train, a partially silvered mirror (90/10) splits the image between the color camera and the two monochrome cameras. In some embodiments, the image is further split between the two monochrome cameras using an interchangeable filter cube, containing a single dichroic mirror and two emission filters optimized for a particular pair of fluorophores or a single ratiometric dye.

Light Sources

In some embodiments, a light source comprises a plurality of light engines. In some embodiments, a light source comprises (i) a first light engine in the plurality of light engines emits a first light for illuminating the target, and (ii) a second light engine in the plurality of light engines emits a second light for exciting a first fluorophore in the target. In some embodiments, a light source comprises a first, second and third light engine. In some embodiments, the third light engine in the plurality of light engines emits a third light for exciting a second fluorophore in the target; and a third detector in the plurality of detectors detects a second fluorescence emitted by the excited second fluorophore, thereby producing a second fluorescence image.

LEDs are the principal light sources for the imaging systems described herein. In some embodiments, arrays of LED chips are organized into functional units termed light engines. In some embodiments, the imaging system comprises a plurality of light engines. In some embodiments, the imaging system comprises 1, 2, 3, 4, 5, 6, 7, 8, 9, 10 or more light engines. In some embodiments, the light engine in the plurality of light engines comprises an array of LED chips. In some embodiments, the plurality of light engines comprises 2, 3, 4, 5, 6, 7, 8, 9, 10, 20, or more high-power LED chips. In some embodiments, the plurality of light engines comprises 2, 3, 4, 5, 6, 7, 8, 9, 10, 20, 30 or more high-power LED chips bonded to a solid substrate. In some embodiments, the first light engine in the plurality of light engines emits a white light. In some embodiments, the LED chips emit white light. Such LED chips for use in the imaging systems of the present invention are readily available from commercial sources in a variety of wavelengths/colors.

Figure 4:
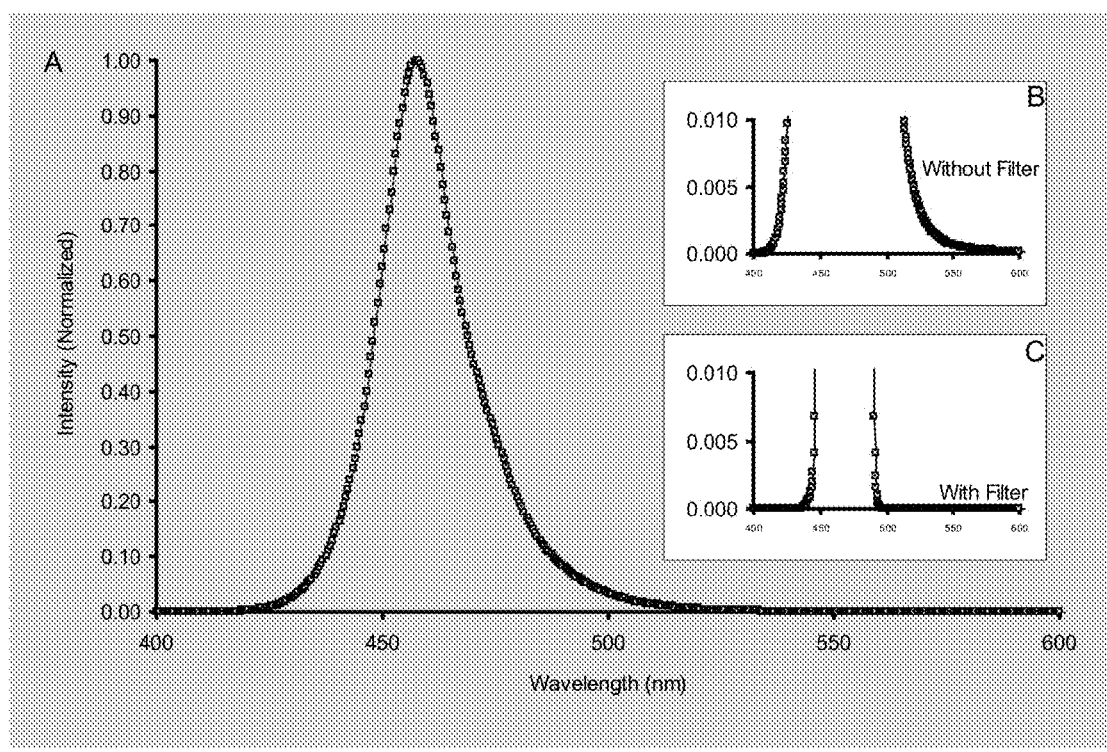
FIGS. 4A-4C provides for exemplary emission spectra of a light engine, in accordance with some embodiments of the present disclosure. A) Emission spectra of a 460 nm LED light engine showing its relatively wide bandwidth. B) Expanded view of the same spectra showing that light emission, although dim, occurs at all wavelengths in the visible spectrum. This off-peak emission is bright enough to interfere with the emission of the target fluorophore and therefore needs to be removed. C) Detail of the same light engine with a narrow band interference filter showing removal of the off-peak emission.

In some embodiments, a light engine consists of the following: 7 high-power LED chips bonded to a copper substrate, collector lens assembly, custom machined housing, and liquid cooling for maximal thermal stability. In some embodiments, power for the light engines is provided by a single channel, current regulated power supply (e.g., a Newport Model 5600). In some embodiments, modulation of the output current is controlled by an external analog input signal (8 kHz bandwidth). In some embodiments, well formed, stable current pulses as narrow as 1 msec and up to 40 amps in amplitude can be generated by the system. In some embodiments, a bank of solid state relays is used to multiplex the single output channel of the power supply to each of the system's light engines. In some embodiments, two, three, four, five or six, or more light engines are energized at a time. In some embodiments, one relay is employed for each light engine. In some embodiments, only one light engine is energized at a time. In some embodiments, two, three, four, five or six, or more relays are employed for each light engine. In some embodiments, two, three, four, five or six, or more light engines are energized at a time. In some embodiments, the output of the light engine used for fluorescence excitation is collimated (i.e., light whose rays are parallel) and filtered using a narrow-band interference filter. In some embodiments, collimation to better than a 12 degree half cone angle is achieved, with out-of-band filter rejection approaching $10^{-6}$ (FIG. 4).

In some embodiments, in an effort to reduce spatial non-uniformity of either single- or mixed-color light distribution a light integrating light pipe (ILP) is employed. Such a pipe can hexagonal or square in cross-section integrating light pipe (PCIL)

In some embodiments, a hexagonal light pipe for homogenizing both light sources ("white-light" and fluorescence) at the specimen plane is connected to the light engine. As used herein, the "hexagonal light pipe" refers to a technique employed to improve the uniformity of illumination at the specimen plane (for example, the surgery location Detectors In some embodiments, multiple detectors are employed to detect a variety of different fluorescent images from a variety of fluorophores as described herein. In some embodiments, a detection unit comprises (i) a first detector in the plurality of detectors detects the reflectance from the target, thereby producing a reflectance image in the plurality of images, and (ii) a second detector in the plurality of detectors detects a first fluorescence emitted by the excited first fluorophore, thereby producing a first fluorescence image. In some embodiments, a detection unit further comprises a third detector in the plurality of detectors. In some embodiments, a third detector in the plurality of detectors detects a second fluorescence emitted by the excited second fluorophore, thereby producing a second fluorescence image. In some embodiments, a fourth third detector in the plurality of detectors detects a third fluorescence emitted by the excited second fluorophore, thereby producing a second fluorescence image.

In some embodiments, the first detector in the plurality of detectors comprises a color camera. In some embodiments, the second detector in the plurality of detectors comprises a first monochrome camera. In some embodiments, the third detector in the plurality of detectors comprises a second monochrome camera. In some embodiments, the fourth detector in the plurality of detectors comprises a third monochrome camera. In some embodiments, the fifth detector in the plurality of detectors comprises a fourth monochrome camera. In some embodiments, the sixth detector in the plurality of detectors comprises a fifth monochrome camera.

In some embodiments, the one camera employs a charge-coupled device (CCD) sensor. In some embodiments, the two cameras each employ a CCD sensor. In some embodiments, the three cameras each employ a CCD sensor. In some embodiments, the form factor, image resolution and maximum camera speed are identical for the two cameras employed. In some embodiments, the form factor, image resolution and maximum camera speed are identical for the three cameras employed.

In some embodiments, the imaging system of the present invention comprises an imaging system comprising three cameras, a color camera and two monochrome cameras, for example but not limited to a Redlake MegaPlus II ES 2020C and ES 2020M, respectively. In some embodiments, the cameras employ a CCD sensor. In some embodiments, the cameras use the same CCD sensor (Kodak KAI-2020), one with a color mask and one without a color mask. In some embodiments, the form factor, image resolution, and maximum camera speed are identical for the three cameras. In some embodiments, the form factor, image resolution (1600×1200 pixels), and maximum camera speed (30 fps) are identical for the three cameras. In some embodiments, use of the same detector assures optimal alignment of the color images and monochrome images. In some embodiments, two high-speed digital interfaces (CameraLink) stream images to the host computer in real-time.

In some embodiments, the optical train comprises a light pipe homogenizer in a light illumination path for producing a uniform distribution of an excitation light across the target.

In some embodiments, the optical train comprises one or more mirrors in a light detection path for splitting lights between or among the plurality of detectors.

In some embodiments, the second light is collimated and filtered before being directed to the target, using a first narrow-band interference filter.

In some embodiments, each of the second light and the third light the second light is collimated (i.e., rays of light made accurately parallel) and filtered before being directed to the target.

In some embodiments, each of the third light and the fourth light the second light is collimated and filtered before being directed to the target.

In some embodiments, the plurality of lights is subjected to polarization in order minimize reflections from the white light reflectance. In some embodiments, the plurality of lights is subjected to dual polarization in order minimize reflections from the white light reflectance.

Display Units

In some embodiments, the allowable display modes vary depending upon the type of fluorophore(s). For example, in some embodiments wherein a single, non-ratiometric probe is employed, images can be displayed in one of three modes: 1) Full color image only (color camera) 2) Fluorescent image only (monochrome camera) 3) Full color image overlayed with fluorescent image (color camera and monochrome camera) (see, FIG. 6). In some embodiments, a foot pedal can be employed with the imaging system which allows a surgeon to quickly toggle between the various display modes without using hands.

In some embodiments, the imaging system further comprises a display unit for displaying an image in the plurality of images. A display unit can include but is not limited to a monitor, television, computer screen/terminal, LCD display, LED display or any other display unit on which an image can be viewed and with can be connect to the imaging system described herein. In some embodiments, the display unit displays the plurality of images by overlying the reflectance image with one or more fluorescence images in real-time.

In some embodiments, the imaging system can be adapted to systems with binocular vision. In some embodiments, the imaging system can be adapted to systems with binocular vision for improved depth of field during surgery.

Control Unit

In some embodiments, the light source unit is controlled by the control unit such that only one light engine in the plurality of light engines is energized at a time.

In some embodiments, the light source unit is controlled by the control unit such that each light engine in the plurality of light engines is energized sequentially.

In some embodiments, the control unit synchronizes the light source unit and the detection unit. In some embodiments, the control unit synchronizes the light source unit and the detection unit such that each light engine in the plurality of light engines is energized sequentially.

In some embodiments, the control unit and the display unit are embedded in a computer. In some embodiments, the control unit and the display unit are part of a computer system or other controller system.

In some embodiments, the control unit is capable of performing the imaging algorithms described herein. In some embodiments, the computer is pre-programmed to run the imaging algorithms.

Connections

One of skill in the microscopic arts would understand how to connect the various components and equipment described herein in order to employ the methods of the present invention.

Imaging Algorithms and Methods

In some embodiments, the reflectance and fluorescence images are displayed side by side. In some embodiments, the reflectance and fluorescence images are displayed alternating on a single monitor. In some embodiments, the reflectance and fluorescence images are displayed overlapping on a single monitor. In some embodiments, the reflectance and fluorescence images are displayed in a pseudocolor such as green, yellow, or aqua, a hue not normally present in tissue, and then superimposed on the color reflectance image. The present disclosure provides the following algorithms for superimposing reflectance and fluorescence images:

TABLE 1

Generalized Algorithm

| DISPLAY ALGORITHM | SINGLE FLUORESCENCE CHANNEL | E 01 |
|---|---|---|
| (Display Pixel)$_{R,G,B}$ = (1 − T) · (ImageA)$_{R,G,B}$ + T · (ImageB)$_{R,G,B}$ | | | where,
T = F/F$_{max}$ (Transparency Factor)
F = Fluorescence intensity from the Monochrome camera
F$_{max}$ = Maximum allowed value of F (either autoscaled from the actual image or preset by the user)
ImageA = RGB Coordinate for Image A
ImageB = RGB Coordinate for Image B As used herein, the phrase "transparency factor" determines what percentage of ImageB relative to ImageA is visible in the final display image. According to the present disclosure, a "transparency factor" value of 0.0 indicates that none of ImageB is visible while a "transparency factor" of 1.0 means that each pixel consists of 100% of ImageB's pixel value. A "transparency factor" of 0.25 indicates that each pixel consists of 25% of ImageB's pixel value plus 75% of ImageA's pixel value. A "transparency factor" of 0.5 indicates that each pixel consists of 50% of ImageB's pixel value plus 50% of ImageA's pixel value. A "transparency factor" of 0.75 indicates that each pixel consists of 75% of ImageB's pixel value plus 25% of ImageA's pixel value.

In some embodiments, algorithms for visualizing one fluorophore are provided. In some embodiments, the present disclosure provides an algorithm for displaying a single fluorescence channel. In some embodiments, in the algorithm for displaying a single fluorescence channel, ImageA is the RGB coordinate of the reflected white light image from the color camera and ImageB is the RGB coordinates of the overlay pseudocolor at maximum intensity.

TABLE 2

Single Fluorescence Channel Algorithm

Figure 6:
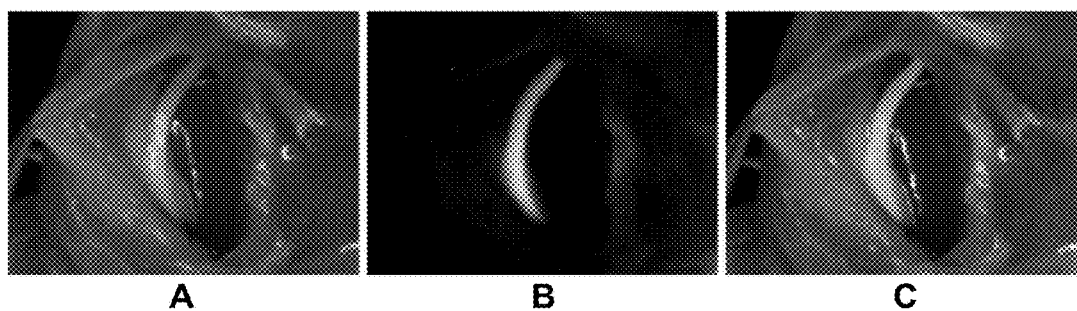
FIG. 6 provides for an example of the three modes of image display for the same field of view, in accordance with some embodiments of the present disclosure. An example of the three modes of image display for the same field of view, a mouse sciatic nerve targeted with FAM This is a cropped view from a larger original image. A) Color image only B) Fluorescent image only C) Combined color and fluorescent image.

| DISPLAY ALGORITHM | SINGLE FLUORESCENCE CHANNEL | EQ 01 |
|---|---|---|
| (Display Pixel)R,G,B = (1 − T) · (Reflectance Pixel)R,G,B + T · (Pseudocolor Pixel)R,G,B | | | where,
Reflectance Pixel = RGB Coordinate from Color camera
Pseudocolor Pixel = RGB Coordinate for overlay color at maximum intensity The RGB coordinate for the "Pseudocolor Pixel" is the brightness coordinate for a given overlay color. By way of non-limiting example, with 8 bit grey-scale images, the "Pseudocolor Pixel" value for the color green would equal 0 for red, 255 for green, and 0 for blue. This corresponds to the brightest RGB coordinate for the color green. A non-limiting example of an image processed by such an algorithm is shown in FIG. 6.

In some embodiments, algorithms for visualizing two fluorophores are provided. In some embodiments, a second channel is added to visualize two fluorophores simultaneously. In some embodiments, the two fluorophores emit distinctly detectable emission spectra. In some embodiments, each fluorophore can be detected separately. In some embodiments, one color fluorophore is employed for a tumor-labeling probe and another color fluorophore is employed for a nerve-homing probe. In some embodiments, the use of two fluorophores allows for the precise resection of diseased tissue (for example tumor tissue) while sparing normal tissue (for example nerve). In some embodiments, the display algorithm for two molecularly independent probes is shown in Table 3 below.

TABLE 3

Dual Fluorescence Algorithm

| DISPLAY ALGORITHM | DUAL FLUORESCENCE CHANNEL | EQ 02 |
|---|---|---|
| (Display)R,G,B = (1 − T1 − T2) · (Reflectance)R,G,B + T1 · (Pseudocolor 1)R,G,B + T2 · (Pseudocolor 2)R,G,B | | | where,
T1 = Transparency factor for fluorescence Ch 1
T2 = Transparency factor for fluorescence Ch 2
Reflectance = Pixel RGB Coordinate from Color camera
Pseudocolor 1 = Pixel RGB Coordinate for overlay color at maximum intensity for fluorescence Ch 1
Pseudocolor 2 = Pixel RGB Coordinate for overlay color at maximum intensity for fluorescence Ch 2

According the dual fluorescence algorithm, T1 and T2 are the transparency factors for the two fluorescence channels respectively, and Pseudocolor Pixels 1 and 2 are the chosen maximum intensity pure colors, for example pure blue=(0, 0, 255) for one channel and pure green=(0, 255, 0) for the other fluorescence channel. Very few pixels if any should have large values for both T1 and T2 simultaneously, but (1−T1−T2) is limited to nonnegative values.

In some embodiments, a category of probes that can be accommodated by dual fluorescence camera systems are probes that shift their emission spectrum from one wavelength range to another upon biochemical activation. The most common type of probes in this category are called FRET probes. FRET probes contain two fluorophores interacting by fluorescence resonance energy transfer (FRET), a mechanism which quenches the shorter-wavelength donor dye while sensitizing its longer-wavelength acceptor partner. Cleavage of the linker between the probes disrupts FRET so that the emission spectrum reverts to that of the donor alone.

The ratio between the two emission bands determines the degree of cleavage while canceling out many factors such as probe concentration, tissue thickness, excitation intensity, absorbances that affect both wavelengths equally, as well as motion artifacts. Emission ratioing can thus significantly increase the sensitivity and specificity of tumor or atherosclerotic plaque detection, for example, justifying the increased complexity of the probe molecules and instrumentation.

In some embodiments, the two fluorophores are donor: acceptor FRET pair or a BRET (bioluminescence resonance energy transfer) pair. Donors can include any appropriate molecules listed herein or known in the art and as such include but are not limited to FITC; Cy3; EGFP; cyan fluorescent protein (CFP); EGFP; 6-FAM; fluorescein, IAE-DANS, EDANS and BODIPY FL. Acceptors can include any appropriate molecules listed herein or known in the art and as such include but are not limited to TRITC; Cy5; Cy3; YFP; 6-FAM; LC Red 640; Alexa Fluor 546; fluorescein; tetramethylrhodamine; Dabcyl (acceptor); BODIPY FL; QSY 7, QSY 9, QSY 21 and BBQ-650 dyes. Exemplary FRET pairs can include but are not limited to CFP:YFP; 6-FAM:Cy5; Cy5:Cy7; Cy5:IRdye800CW; FITC:TRITC; Cy3:Cy5; EGFP:Cy3; EGFP:YFP; 6-FAM:LC Red 640 or Alexa Fluor 546; fluorescein:tetramethylrhodamine; IAE-DANS:fluorescein; EDANS:Dabcyl; fluorescein:fluorescein; BODIPY FL:BODIPY FL; and fluorescein:QSY 7 and QSY 9 dyes.

In some embodiments, the cleavage of the FRET probe occurs intracellular and/or extracellularly. FRET probes can be designed with particular cleavage sequences. In some embodiments, cleavage can occur based on pH, as well as based on other environmental factors in the area being imaged. Examples of pH-sensitive linkages include acetals, ketals, activated amides such as amides of 2,3-dimethylmaleamic acid, vinyl ether, other activated ethers and esters such as enol or silyl ethers or esters, imines, iminiums, enamines, carbamates, hydrazones, and other linkages. In some embodiments, FRET probes can be cleaved by proteases and nucleases, as well as reactive oxygen species such as hydrogen peroxide. Exemplary proteases and the sequences which the proteases cleave include but are not limited to MMPs (PLGLAG and PLGC(met)AG, elastases (RLQLK(acetyl)L, plasmin, thrombin, DPRSFL, PPRSFL or PLGC(Me)AG, 6-aminohexanoyl, 5-amino-3-oxapentanoyl, p-amido-benzyl ether (such as for example Val-Cit-(p-amido)benzyloxycarbonyl (Val-Cit-PAB)) DPRSFL, PPRSFL or PLGC(Me)AG, MMP 2,9 (PLGLAG and/or PLGC(met)AG), RS-(Cit)-G-(homoF)-YLY, PLGLEEA, CRPAHLRDSG, SLAYYTA, NISDLTAG, PPSSLRVT, SGESLSNLTA, RIGFLR, elastase cleavable (or substantially specific sequence such as for example RLQLK(acetyl)L, plasmin cleavable (such as for example RLQLKL), thrombin selective (such as for example DPRSFL, PPRSFL, Norleucine-TPRSFL), chymase cleavable (or substantially specific sequence such as for example GVAY|SGA), urokinase-type plasminogen activator (uPA; such as for example YGRAAA), tissue plasminogen activator (tPA) cleavable (or substantially specific sequence such as for example YGRAAA) or uPA cleavable (or substantially specific sequence such as for example YGPRNR) and/or combinations thereof. One of skill could determine which cleavage agent or agents would be expressed in the diseased tissue and appropriately design the proper probes for use with the imaging system and methods described herein.

In some embodiments, the high speed alternation requires electronic switching between the light engines. As used herein, the phrase "electronic switching" refers to a light engine being turned on and off. In some embodiments, high speed alternation requires electronic switching at a rate of <1 msec. In some embodiments, the electronic switching is controlled by the control unit. In some embodiments, the light engine that can be employed is any light source capable of high speed switching, i.e., high speed "on and off". Exemplary electronic switching light engines include but are not limited to LEDs, lasers and pulsed xenon flash lamps. In some embodiments, the white light and fluorescence electronic switching are individually controlled.

The present disclosure provides three methods for displaying "Overlay Ratio Pixel" and each of the three methods are described in detail below.

TABLE 4

Ratiometric Method 1

| DISPLAY ALGORITHM | RATIOMETRIC METHOD 1 | EQ 03 |
| --- | --- | --- |
| (Display Pixel)$_{R,G,B}$ = (Ratio Pixel)$_{R,G,B}$ | | |

Where,
Ratio Pixel = RGB Coordinate based on ratio of the two fluorescence channels (see below for details)

Figure 1:
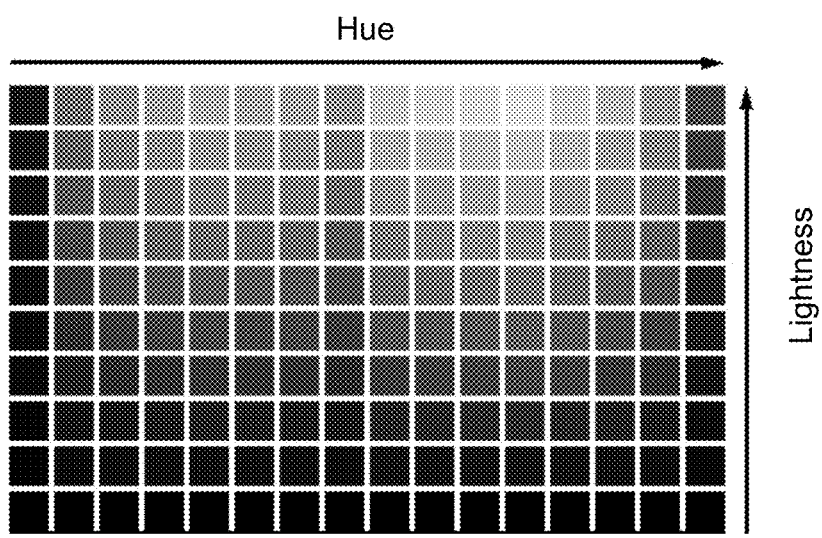
FIG. 1 provides for a custom lookup table (LUT) used to implement HSL to RGB conversion for ratiometric display. Custom lookup table (LUT) used to implement HSL to RGB conversion for ratiometric display. Hue (H) and Lightness (L) are the two input variables for the lookup table. Hue encodes the mathematical ratio of the two fluorescence channels and increases from left to right (the color red being the highest ratio). Lightness corresponds to the intensity of one of the fluorescence channels (usually the brightest one) and increases from top to bottom. Saturation (S) is maximized for all output colors and therefore can be considered a constant. This 16×10 LUT is loaded into host memory during program initialization and is expanded to a 256×256 LUT (using linear interpolation) for use in the image processing pipeline. For this particular implementation of the LUT, all inputs are 8 bits (0-255) but higher bit values are possible, limited only by the memory size of the computer.
Figure 7:
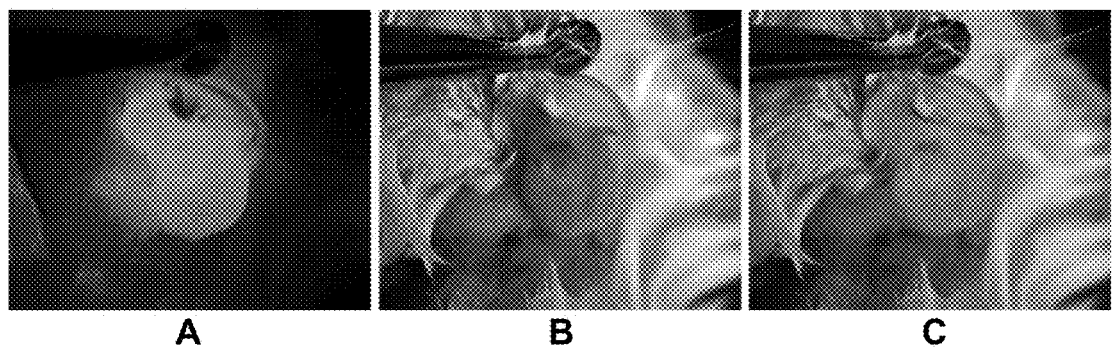
FIG. 7 provides examples of the three types of algorithms used to display ratiometric images, in accordance with some embodiments of the present disclosure. Examples of the three types of algorithms used to display ratiometric images. The orange zone is a tumor showing a high ratio of Cy5 to Cy7 emissions. These views are cropped from larger original images. A) Method 1 with no reflected white light image. B) Method 2 using an HSL to RGB color space converter with black and white overlay. C) Method 3 uses maximum pseudocolor brightness with a black and white overlay (gamma=3.0).

Ratiometric Method 1 as provided herein comprises an algorithm where the ratio image is not overlayed with the white light reflectance image and hence there is no transparency factor in the formula. According to Ratiometric Method 1, the ratio image is based solely on the ratio between the two fluorescence images and the intensity of one of these images. The ratio is encoded as a spectrum of colors from blue to red, with blue corresponding to low ratio values and red corresponding to high ones. The hue of the "Ratio Pixel" coordinate is determined by its ratio and the lightness (brightness) is determined by the intensity of one of these channels (usually the brighter one). This formula is essentially a color space conversion algorithm, converting HSL color space to RGB color space, where H stands for hue (the ratio), S stands for saturation (set to maximum) and L stands for lightness (the intensity of one of the fluorescence channels). The conversion process is implemented using a software lookup table (LUT) with two input variables (H and L) and one output variable, the RGB display coordinate. According to the present methods, a custom LUT to implement the HSL conversion process is used instead of using one of the established algebraic transformations. The established transformations all suffer from the same flaw: they map ratios to linear ramps in R,G,B coordinates, which is incompatible with how humans actually perceive color. In order to more closely match the human visual system, a custom color conversion LUT was prepared, as shown in FIG. 1. A non-limiting example of an image processed using this algorithm is shown in FIG. 7, panel A.

TABLE 5

Ratiometric Method 2

| DISPLAY ALGORITHM | RATIOMETRIC METHOD 2 | EQ 04 |
| --- | --- | --- |
| (Display Pixel)$_{R,G,B}$ = (1 − T) · (BW Reflectance Pixel)$_{R,G,B}$ + T · (Ratio Pixel)$_{R,G,B}$ | | | where,
BW Reflectance Pixel = RGB Coordinate for black and white version of Color camera
Ratio Pixel = RGB Coordinate based on ratio of the fluorescence channels (see below for details)

Ratiometric Method 2 as provided herein, provides an algorithm wherein a pseudocolor, ratio encoded image is overlayed on top of a black and white (BW) version of the white light reflection image. The transparency factor is calculated in the same manner as for the Generalized formula above (see "Generalized Formula"). The ratio image is encoded as a spectrum of colors from blue to red, with blue corresponding to low ratio and red corresponding to high one. Because the ratio encoded image can display any color in the spectrum, the ratio image is overlayed on top of a black and white representation of the color reflected image. The coordinates for the "Ratio Pixel" parameter are calculated using the same custom LUT shown in FIG. 1. As in Ratiometric Method 2, the H input corresponds to the ratio between the two fluorescent cameras. However, the value for the L input is based on the black and white reflected image instead of one of the fluorescent channels. A non-limiting example of an image encoded using this algorithm is shown in FIG. 7, panel B.

TABLE 6

Ratiometric Method 3

DISPLAY ALGORITHM    RATIOMETRIC METHOD 3    EQ 05
(Display Pixel)$_{R,G,B}$ = (1 − T$^\gamma$) · (BW Reflectance Pixel)$_{R,G,B}$ + T$^\gamma$ · (Ratio Pixel)$_{R,G,B}$ where,
γ = Gamma Factor - values greater than 1 de-emphasize dim fluorescent pixels.
BW Reflectance Pixel = RGB Coordinate for black and white version of Color camera
Ratio Pixel = RGB Coordinate for overlay color at maximum intensity Ratiometric Method 3 as provided herein provides an algorithm wherein a pseudocolor, ratio encoded image is overlayed on top of a black and white (BW) version of the white light reflection image. The transparency factor is calculated as shown previously (see "Generalized Formula"). The ratio image is encoded as a spectrum of colors from blue to red, with blue corresponding to low ratio and red corresponding to high one. The coordinate for the "Ratio Pixel" parameter is the maximum intensity for of hue determined by this ratio. The hue is calculated using the custom LUT shown in FIG. 1, where H equals the ratio between the two fluorescent channels and L is set to maximum (255). A non-limiting example of an image encoded using this algorithm is shown in FIG. 7, panel C.

In some embodiments, the above methods and imaging algorithms described herein can be employed to allow for simultaneous and/or overlapping viewing of white light and fluorescent images. In some embodiments, a white-light image (which provides the normal landmarks that surgeons are accustomed to seeing) and a fluorescence image for indicating the location of targeted fluorescence molecules (fluorophore) can be viewed simultaneously. In some embodiments, a white-light image (which provides the normal landmarks that surgeons are accustomed to seeing) and a fluorescence image for indicating the location of targeted fluorescence molecules (fluorophore) can be viewed in alternating view frames or side-by-side on a monitor unit. In some embodiments, the high speed alternation between white light and fluorescence allows for real-time video streaming of the target area. In some embodiments, the alternation rate is above 60 Hz. In some embodiments, the alternation above 60 Hz reduces and/or eliminates visual flicker.

In some embodiments, the high speed alternation requires electronic switching between the light engines. As used herein, the phrase "electronic switching" refers to a light engine being turned on and off. In some embodiments, high speed alternation requires electronic switching at a rate of <1 msec. In some embodiments, the electronic switching is controlled by the control unit. In some embodiments, the light engine that can be employed is any light source capable of high speed switching, i.e., high speed "on and off". Exemplary electronic switching light engines include but are not limited to LEDs, lasers and pulsed xenon flash lamps. In some embodiments, the white light and fluorescence electronic switching are individually controlled.

Fluorescence Guided Surgery

The present invention provides fluorescence-immuno-tissue detection and fluorescence guided surgery. In some embodiments, an image processing method for fluorescence guided surgery. In some embodiments, the present invention employs surgical instruments useful for performing a tissue manipulation procedure. As used herein, the term "surgical instruments" refer to any medical instruments, devices and/or tools, in all types and sizes that are used in a surgical procedure. Exemplary surgical instruments include, but are not limited to, medical instruments comprising an electrocautery tip and/or a fiberoptic laser delivery tip, cutting instruments including but not limited to scissors, scalpels, surgical knives, and blades, grasping instruments including but not limited to forceps and clamps, tissue marking devices, probes, and other instruments including, but not limited to, curettes, dermatomes, dilators, hemostats, photocoagulators, retractors, snares, and trephins.

In some embodiments, the surgical instruments are provided as single-use devices, being designed to be disposed of after one single use. In yet another preferred embodiment, the surgical instruments are provided as reusable devices capable of repeated cleaning and sterilization. As used herein, the term "cleaning and sterilization" refers to any acts and procedures that make the surgical instruments free of live bacteria or other microorganisms, usually by heat or any chemical means, and yet maintains the property of emitting a detectable fluorescent signal when excited by light.

In some embodiments, the one or more fluorescence images comprise a first fluorescence image.

In some embodiments, the one or more fluorescence images comprise a first fluorescence image and a second fluorescence image.

In some embodiments, the one or more fluorescence images comprise more than two fluorescence images.

In some embodiments, the RGB coordinate of a fluorescence image or a factored fluorescence image is a brightness coordinate for a given overlay color.

In some embodiments, the image processing method further comprises displaying the display image in a display unit.

In some embodiments, the image processing method for fluorescence guided surgery comprise a computer system having one or more processors and memory storing one or more programs executed by the one or more processors: (A) acquiring a plurality of images using a detection unit, wherein the plurality of images comprises two fluorescence images; (B) generating a ratio image, wherein a ratio pixel coordinate of the ratio image is determined based on a hue value and a brightness value, and (C) generating a display image by establishing a display RGB coordinate, wherein the display RGB coordinate is determined by using a lookup table with the hue value and the brightness as inputs.

In some embodiments, a ratio pixel coordinate of the ratio image is determined based on a hue value and a brightness value, wherein (i) the hue value is determined based on a ratio of the two fluorescence images, and (ii) the brightness value is determined based on an intensity of one of the two fluorescence images.

In some embodiments, the plurality of images comprises a black and white reflectance image and the method further comprises (D) determining a transparency factor prior to the generating the display image, wherein the transparency factor is a ratio of a fluorescence intensity of one of the two fluorescence images divided by a maximum allowed fluorescence intensity of the corresponding fluorescence image of the two fluorescence images; and (E) factoring RGB coordinates of the reflectance image and the ratio image, subsequent to the generating the ratio image, producing a plurality of factored RGB coordinates.

In some embodiments, when producing a plurality factored RGB coordinate wherein (i) a factored RGB coordinate for the ratio image is the product of a RGB coordinate of the ratio image times the transparency factor, and (ii) a factored RGB coordinate for the reflectance image is the product of a RGB coordinate of the reflectance image times a predetermined constant minus the transparency factor, wherein the transparency factor does not exceed the predetermined constant, wherein the display RGB coordinate equals to a sum of the plurality of factored RGB coordinates.

In some embodiments, the plurality of images comprises a black and white reflectance image and the method further comprises (D) determining a transparency factor prior to the generating the display image, wherein the transparency factor is a ratio of a fluorescence intensity of one of the two fluorescence images divided by a maximum allowed fluorescence intensity of the corresponding fluorescence image of the two fluorescence images; (E) determining a gamma factor; and (F) factoring RGB coordinates of the reflectance image and the ratio image, subsequent to the generating the ratio image, producing a plurality of factored RGB coordinates.

In some embodiments, the producing a plurality of factored RGB coordinates occurs wherein (i) a factored RGB coordinate for the ratio image is the product of a RGB coordinate of the ratio image times the transparency factor to the power of the gamma factor, and (ii) a factored RGB coordinate for the reflectance image is the product of a RGB coordinate of the reflectance image times a predetermined constant minus the transparency factor to the power of the gamma factor, wherein the transparency factor to the power of the gamma factor does not exceed the predetermined constant, wherein the display RGB coordinate equals to a sum of the plurality of factored RGB coordinates.

Light Homogenization

Figure 3:
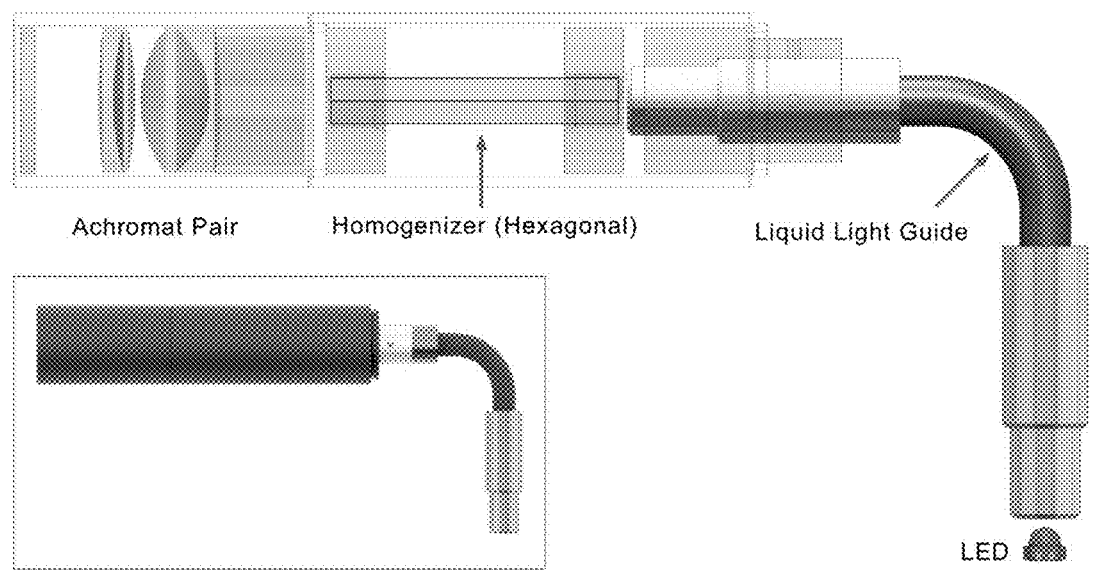
FIG. 3 provides for a diagram of the optical train used to deliver the fluorescent excitation light, in accordance with some embodiments of the present disclosure. Diagram of the optical train used to deliver the fluorescent excitation light to the animal indicating the position of the light pipe homogenizer rod used to ensure a uniform field of illumination. Non-uniform light from the liquid light guide is mechanically coupled into the homogenizing rod whose NA roughly matches that of the light guide. Following total internal reflection, the light distribution across the output face of the rod is uniform to better than 95%. The output face of the homogenizer is re-imaged into the specimen plane using a pair achromat lens. The last component in the optical train is a glass window used to protect the optical assembly.

In some embodiments, a uniform distribution of excitation light across the specimen plane is achieved for proper interpretation of the fluorescence image by the surgeon. In some embodiments, high uniformity is achieved by using a light pipe homogenizing rod in the fluorescent delivery light path (FIG. 3). In some embodiments, light pipe homogenizers utilize total internal reflection to scramble and homogenize non-uniform light sources. In some embodiments, a light pipe has a square cross-section a hexagonal cross-section. In some embodiments, a light pipe with a square cross-section or hexagonal cross-section is employed. In some embodiments, a light pipe that does not have a circular cross-section is employed. Since uniformity is maximal at the output face, in some embodiments, a pair of achromat lens re-image the rod's output face into the surgical field. In some embodiments, uniformity of greater than 80%, 85%, 90%, 95% or 99% can be achieved at the specimen plane. In some embodiments, uniformity of greater than 95% can be achieved at the specimen plane.

Fluorescence and Fluorescence Ratios

With the methods described in the present invention, any of a variety of fluorophores that can be used with the imaging system and a variety of excitation and emission wavelengths can be employed with the imaging system and methods described herein, including but not limited to the entire spectrum from the UV to the infrared is available for fluorophores in excitation and/or emission spectra. In some embodiments, one fluorophore can be detected. In some embodiments, 2, 3, or 4, or more fluorophores can be detected simultaneously. In some embodiments, 2 fluorophores can be detected simultaneously. In some embodiments, 3 fluorophores can be detected simultaneously. In some embodiments, 4 fluorophores can be detected simultaneously.

The fluorescent signal can emanates from any conventional fluorescence materials and/or dyes, also known as fluorophores. As used herein, the term "fluorophore" is analogous to a chromophore and is a functional group in a molecule which will absorb energy of a specific wavelength and re-emit energy at a different (but equally specific) wavelength. The amount and wavelength of the emitted energy depend on both the fluorophore and the chemical environment of the fluorophore. Many natural and synthetic compounds that exhibit fluorescence and/or fluorophores are known in the art and can be used in the present invention.

In some embodiments, a number of fluorescent molecules can be employed with the methods of the present disclosure. In some embodiments, the fluorophore exhibits green fluorescence (such as for example 494 nm/519 nm), orange fluorescence (such as for example 554 nm/570 nm), red fluorescence (such as for example 590 nm/617 nm), or far red fluorescence (such as for example 651 nm/672 nm) excitation/emission spectra. In some embodiments, the fluorophore is a fluorophore with excitation and emission spectra in the range of about 350 nm to about 775 nm. In some embodiments the excitation and emission spectra are about 346 nm/446 nm, about 494 nm/519 nm, about 554 nm/570 nm, about 555 nm/572 nm, about 590 nm/617 nm, about 651 nm/672 nm, about 679 nm/702 nm or about 749 nm/775 nm. In some embodiments, the fluorophore can include but is not limited to AlexaFluor 3, AlexaFluor 5, AlexaFluor 350, AlexaFluor 405, AlexaFluor 430, AlexaFluor 488, AlexaFluor 500, AlexaFluor 514, AlexaFluor 532, AlexaFluor 546, AlexaFluor 555, AlexaFluor 568, AlexaFluor 594, AlexaFluor 610, AlexaFluor 633, AlexaFluor 647, AlexaFluor 660, AlexaFluor 680, AlexaFluor 700, and AlexaFluor 750 (Molecular Probes AlexaFluor dyes, available from Life Technologies, Inc. (USA)). In some embodiments, the fluorophore can include but is not limited to Cy dyes, including Cy2, Cy3, Cy3B, Cy3.5, Cy5, Cy5.5 and Cy7 (available from GE Life Sciences or Lumiprobes). In some embodiments the fluorophore can include but is not limited to DyLight 350, DyLight 405, DyLight 488, DyLight 550, DyLight 594, DyLight 633, DyLight 650, DyLight 680, DyLight 750 and DyLight 800 (available from Thermo Scientific (USA)). In some embodiments, the fluorophore can include but is not limited to a FluoProbes 390, FluoProbes 488, FluoProbes 532, FluoProbes 547H, FluoProbes 594, FluoProbes 647H, FluoProbes 682, FluoProbes 752 and FluoProbes 782, AMCA, DEAC (7-Diethylaminocoumarin-3-carboxylic acid); 7-Hydroxy-4-methylcoumarin-3; 7-Hydroxycoumarin-3; MCA (7-Methoxycoumarin-4-acetic acid); 7-Methoxycoumarin-3; AMF (4'-(Aminomethyl)fluorescein); 5-DTAF (5-(4,6-Dichlorotriazinyl)aminofluorescein); 6-DTAF (6-(4,6-Dichlorotriazinyl)aminofluorescein); 6-FAM (6-Carboxyfluorescein), 5(6)-FAM cadaverine;

5-FAM cadaverine; 5(6)-FAM ethylenediamme; 5-FAM ethylenediamme; 5-FITC (FITC Isomer I; fluorescein-5-isothiocyanate); 5-FITC cadaverin; Fluorescein-5-maleimide; 5-IAF (5-Iodoacetamidofluorescein); 6-JOE (6-Carboxy-4',5'-dichloro-2',7'-dimethoxyfluorescein); 5-CR110 (5-Carboxyrhodamine 110); 6-CR110 (6-Carboxyrhodamine 110); 5-CR6G (5-Carboxyrhodamine 6G); 6-CR6G (6-Carboxyrhodamine 6G); 5(6)-Caroxyrhodamine 6G cadaverine; 5(6)-Caroxyrhodamine 6G ethylenediamme; 5-ROX (5-Carboxy-X-rhodamine); 6-ROX (6-Carboxy-X-rhodamine); 5-TAMRA (5-Carboxytetramethylrhodamine); 6-TAMRA (6-Carboxytetramethylrhodamine); 5-TAMRA cadaverine; 6-TAMRA cadaverine; 5-TAMRA ethylenediamme; 6-TAMRA ethylenediamme; 5-TMR C6 malemide; 6-TMR C6 malemide; TR C2 malemide; TR cadaverine; 5-TRITC; G isomer (Tetramethylrhodamine-5-isothiocyanate); 6-TRITC; R isomer (Tetramethylrhodamine-6-isothiocyanate); Dansyl cadaverine (5-Dimethylaminonaphthalene-1-(N-(5-aminopentyl))sulfonamide); EDANS C2 maleimide; fluorescamine; NBD; and pyrromethene and derivatives thereof.

In some embodiments, the fluorophore is biocompatible, allows deep tissue penetration, and limits tissue autofluorescence when used for biomedical imaging.

In some embodiments, the fluorescent signal is excited by broad spectrum lights, UV, far red spectrum, near infrared spectrum, and any other exciting sources known in the art.

In some embodiments, the ratio of the two fluorescence images is encoded as a spectrum of colors.

In some embodiments, the spectrum of colors is from blue to red.

In some embodiments, the spectrum of colors is from blue to red, with blue corresponding to low ratio values and red corresponding to high ratio values. In some embodiments, blue refers to the lowest ratio values and red refers to the highest ratio values.

Probes

In some embodiments, the methods described herein employ one or more fluorescently labeled probes. In some embodiments, the fluorescently labeled probes are fluorescently labeled immunoconjugates. The term "immunoconjugates" as used herein refers to antibodies and fragments thereof (including Fc and Fab fragments), but also includes any protein substance produced in the blood or tissues in response to a specific antigen, such as a bacterium or a toxin, that destroys or weakens bacteria and neutralizes organic poisons, thus forming the basis of immunity, or an immunoglobulin present in the blood serum or body fluids as a result of antigenic stimulus and interacting only with the antigen that induced it or with an antigen closely related to it. In some embodiments, immunoconjugates used in the methods disclosed herein is a monoclonal antibody capable of targeting cellular receptors and/or proteins specifically expressed or over-expressed by tissue of interest. In some embodiments, the tissue of interest is a diseased tissue capable of resection through a surgical process. In some embodiments, the tissue is tumor or cancerous tissue, including metastatic tissue. In some embodiments, the detection refers to fluorescent imaging of target tissues and/or tumors. In some embodiments, the detection refers to tissue involved in inflammation, diabetes, cardiovascular diseases (including, for example, Atherosclerosis), neurodegenerative disorders and cancer.

In some embodiments, the methods described herein employ one or more fluorescently labeled nucleic acid based probes. In some embodiments, the fluorescently labeled nucleic acid based probes are fluorescently labeled polynucleotides or derivatives thereof. The term "nucleic acid probe" as used herein refers to polynucleotides (including DNAs and/or RNAs), siRNAs, PNAs, LNAs, aptamers as well as any other modified nucleic acid based molecules. Such modifications can include 2'fluoro (2'-Deoxy-2'-fluoro-nucleosides) modifications, LNAs (locked nucleic acids), PNAs (peptide nucleic acids), ZNAs (Zip Nucleic Acids), morpholinos, methylphosphonates, phosphoramidates, polycationic conjugates and 2'pyrene modifications. In some embodiments, the fluorescently nucleic acid based probes used in the methods disclosed herein is capable of effecting and/or targeting cellular receptors and/or proteins specifically expressed or over-expressed by tissue of interest. In some embodiments, the tissue of interest is a diseased tissue capable of resection through a surgical process. In some embodiments, the tissue is tumor or cancerous tissue, including metastatic tissue. In some embodiments, the detection refers to fluorescent imaging of target tissues and/or tumors. In some embodiments, the detection refers to tissue involved in inflammation, diabetes, cardiovascular diseases (including, for example, Atherosclerosis), neurodegenerative disorders and cancer.

In some embodiments, other immunoconjugates, and functional fragments thereof, that are capable of targeting tissues of interest, can also be used in with the methods of the present disclosure. In some embodiments, immunoconjugates and functional fragments thereof, can be used for therapeutic, diagnostic and/or detection purposes. In some embodiments, the detection refers to fluorescent imaging of target tissues and/or tumors. In some embodiments, the detection refers to tissue involved in inflammation, diabetes, cardiovascular diseases (including, for example, Atherosclerosis), neurodegenerative disorders and cancer.

In some embodiments, the fluorescently labeled immunconjugate detects a receptor differentially expressed on a neoplastic cell as compared to a non-neoplastic cell. In some embodiments, the neoplastic cell includes but is not limited to breast, prostate, liver, colon, lung, pancreas, stomach, brain, liver, kidney, head, neck, and/or bladder. In some embodiments, the receptor is any receptor known by those of skill in the art to be differentially expressed in cancer versus normal cells. In some embodiments, the receptor a receptor selected from but not limited to G-protein coupled receptors (GPCRs), androgen receptors (ARs), estrogen receptors (ERs), leptin receptors (LRs), growth hormone receptors (GHRs), transforming growth factor receptors (TGFs; including for example but not limited to TGFβ1, TGFβ2 and TGFβ3), epidermal growth factor receptors (EGFRs), HER2/neu receptors, breast cancer associated receptors (including for example but not limited to BRCA1 and BRCA2 receptors), ErbB receptors, ErbB2 receptors, epidermal growth factor receptors (EGFRs), insulin like growth factor receptors (ILGFRs), HGF/Met receptors, tyrosine kinase receptors, pattern recognition receptors (PRRs), Toll-like receptors (TLRs) pathogen-associated molecular patterns (PAMP), killer activated and killer inhibitor receptors (KARs and KIRs), complement receptors, Fc receptors, B-cell receptors, T-cell receptors, cytokine receptors, RAGE, BTLA, protease activate receptors (PARs), nuclear receptors (including for example but not limited to PPARs), mineralocorticoid receptors, platelet ADP receptors, APJ receptor, muscarinic receptors (including for example but not limited to muscarinic acteylcholine receptor M2, M3 muscarinic receptor), glucorticoid receptors, adrenergic receptors, scavenger receptors, calcium sensing receptor (CaR), angiotension II receptor, bile acid receptors, corticosteroid receptors, Protease-activated receptors (PARs), interleukin receptors (including for example, but not limited to interleukin 1 receptors), AMPA receptors, insulin receptors, glucose receptors, cannabinoid receptors, chemokine receptors, N-methyl-D-aspartate (NDMA) receptors, adenosine receptors, peripheral benzodiazepine receptors, sigma-1 receptor, Trk receptors (including for example but not limited to TrkB receptor), nuclear hormone receptors, nicotinic receptors, nicotinic acetylcholine receptors (including for example but not limited to α4β2 and IgG receptors) and integrins. In some embodiments, the immunoconjugate is a ligand capable of binding to αvβ3 or αvβ5. In some embodiments, the immunoconjugate is a ligand capable of binding to αvβ3.

As used herein, the term "tissue of interest" refers to any bodily tissues, organs, glands, cells that are in either normal or defected conditions and can include but is not limited to breast, prostate, liver, colon, lung, pancreas, stomach, brain, liver, kidney, head, neck, and/or bladder. In some preferred embodiments, the tissue is a tumor. As used herein, the term "tumor" refers to an abnormal growth of tissue resulting from uncontrolled, progressive multiplication of cells and serving no physiological, but rather pathological, functions.

As used herein, the term "tissue of interest" can include neoplasms and other tumors at a variety of stages, including a metastasized tumor that has spread to distant sites (liver or lung) or to regional sites (lymph nodes). The terms "neoplasm" or "neoplasia" and derivatives thereof as used herein, include any non-normal or non-standard cellular growth. Neoplasms can include tumors and cancers of any variety of stages, from benign to metastatic. Neoplasms can be primary or metastatic growths and can occur anywhere in a subject. Neoplasms can include neoplasms of the lung, skin, lymph nodes, brain, nerves, muscle, breast, prostate, testis, pancreases, liver, kidneys, stomach, muscle, thyroid, parathyroid and bone. Neoplasms can be solid and non-solid tumors.

In some embodiments, the fluorescently labeled immunoconjugate and associated imaging equipment and instruments can be used for diagnostic purposes or therapeutic purposes to image the site(s). In some embodiments, confirmation of distant disease and directed biopsies based on fluorescence can be performed. In some embodiments, dissection and sampling of the lymph nodes or fluorescently guided biopsies of distant metastatic sites can be performed using the methods of the present invention. In some embodiments, the present invention provides a method of intraoperative tissue detection, manipulation and/or removal. Such method comprises administering one or more fluorescently labeled immunoconjugates, such as antibodies, to a subject, said immunoconjugates being capable of targeting the tissue of interest, visualizing said tissue tagged with said one or more fluorescently labeled immunoconjugates with a visualization instrument, and performing a tissue manipulation procedure according to the imaging system methods as disclosed herein.

In some embodiments, the present disclosure also provides a method of determining the prognosis of a disease condition in a tissue in vivo comprising administering to a patient a detection effective amount of a fluorescently labeled immunoconjugate specific for the disease condition in the tissue, and visualizing and comparing a fluorescent pattern in the disease tissue with a fluorescent pattern in normal tissue to determine the prognosis of the disease condition. As used herein, the term "prognosis" refers to a predicted and/or expected course of a disease including various developments, changes and outcomes of the disease. As used herein, the term "detection effective amount'" refers to any amount of immunoconjugate that is labeled with an amount of fluorophore so that the labeled immunoconjugate can be visualized and imaged using the imaging methods described herein.

In some embodiments, the present disclosure also provides methods for monitoring therapy of a disease condition with a combination of fluorophore labeled and unlabeled immunoconjugates for both therapeutic and diagnostic purposes. In one preferred embodiment, a treatment effective amount of an unlabeled immunconjugate specific for a disease tissue and/or tumor, and a detection effective amount of a fluorophore labeled same immunoconjugate are administered, simultaneously or at approximately the same time, to a patient for both treatment and detection purposes. In some embodiments, the unlabeled and fluorophore labeled immunoconjugate are prepared in a single preparation. As used herein, the term "treatment effective amount" refers to any amount of immunoconjugate that has therapeutic effects on the disease tissue and/or tumor such that the disease tissue becomes normal tissue gradually and/or eventually, and the tumor cells are killed or dead with the tumor size reduced and/or disappeared.

In some embodiments, the immunofluorescent guided surgery methods as described in the present disclosure provide for improved identification of residual tumor within the resection bed. In some embodiments, methods of detecting the tumor beneath the outer level of surrounding tissue which is often the source of residual tumor margin remaining following surgery is improved. In some embodiments, the present invention allows rapid assessment of tumor margins after tumor ablation. In some embodiments, the lymphatic drainage basins can be assessed intraoperatively to identify nests of tumor within or extending out of lymph nodes. In some embodiments, routine histology combined with confocal fluorescence can improve the identification of positive or close margins pathologies. In some embodiments, the present disclosure provides methods for immunofluorescence detection and microscopic assisted resection guided by immunofluorescence for surgical guidance.

In some embodiments, the present disclosure provides a method of increasing the intraoperative visualization of tumors comprising determining one or more immunoconjugates specific to a target tumor, conjugating a fluorophore to said antibodies, and ensuring that fluorescence of surrounding tissue is minimized so as to increase the contrast between said target tumor and said surrounding tissue.

In some embodiments, the present disclosure provides a visualization molecule for intraoperative tumor visualization comprising an immunoconjugate specific to an antigen expressed or overexpressed on tumor cells conjugated to a fluorophore with known excitation and emission wavelengths. In some embodiments, the fluorophore emits light in the near infrared spectrum. In some embodiments, the immunoconjugate is sequestered by the targeted tumor such that the target tumor fluoresces across the depth of the target tumor. In some embodiments, the immunoconjugate binds to the target tumor with greater affinity than to surrounding non-tumor tissue.

In some embodiments, the immunofluorescent detection according to the present disclosure provides a means of diagnosing and/or detecting cancers. In some embodiments, fluorescent imaging neoplasm detection according to the present invention thus offers a specific and sensitive tool for the detection and resection of cancer. In some embodiments, fluorescent imaging tissue detection according to the present invention may be employed in the planning of radiotherapy ports for patients with cancer or employed as part of a treatment regimen.

System Controller

The imaging systems described herein can include a system controller portion. In some embodiments the system controller is a computer. Regardless of the particular configuration for computer systems employed with the imaging systems disclosed herein, the computer system may employ one or more memories or memory modules configured to store program instructions for fluorescent imaging and obtaining a three-dimensional representation of a light source located inside a subject and other functions of the present invention described herein. Such memory or memories may also be configured to store data structures, imaging data, or other specific non-program information described herein.

As such information and program instructions may be employed to implement the systems, methods and algorithms disclosed herein, the present invention relates to machine-readable media that include program instructions, state information, etc. for performing various operations and/or algorithms described herein. Examples of machine-readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). In some embodiments, the present disclosure also contemplates employing a carrier wave traveling over an appropriate medium such as airwaves, optical lines, electric lines, etc. as part of the contemplated computer system. Examples of program instructions include both machine code, such as produced by a compiler, and files containing higher level code that may be executed by the computer using an interpreter.

Figure 5:
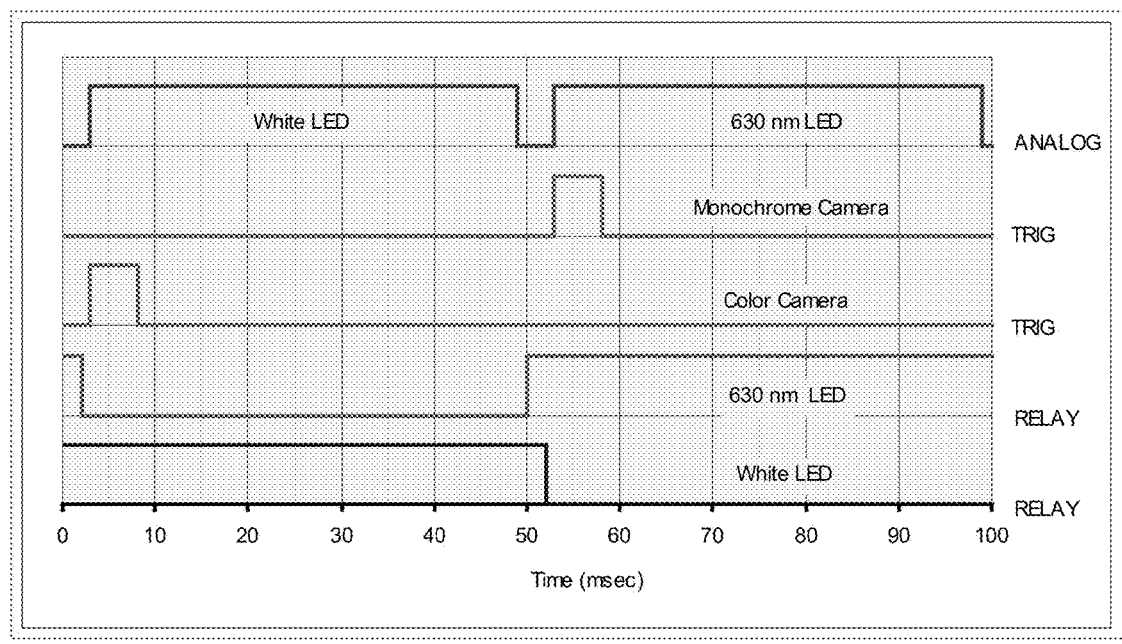
FIG. 5 provides for example of timing signals, in accordance with some embodiments of the present disclosure. Example of timing signals generated by National Instruments 6229 for a two camera system. The "ANALOG" channel controls the timing and brightness for system's two light engines (the white LED, and a 630 nm LED for use with the fluorophore Cy5). Brightness is encoded by the amplitude of this analog waveform. The two "TRIG" channels initiate a single image capture by each of the system's two cameras. Finally, the "RELAY" channels determine which of the system's light engines is currently active. Only one light engine is active at a time, yielding an overall update frequency of 10 Hz. In practice higher frequencies are desirable to minimize motion artifact and latency to the monitor. Increasing the update frequency beyond the psychophysical flicker-fusion frequency for humans (approximately 60 Hz) eliminates the stroboscoptic light leaking from the field of illumination.

In some embodiments, a single host computer provides the user interface for the surgeon. In some embodiments, the computer initializes all hardware, synchronizes the cameras and LEDs, captures the live video streams, overlays the two images in host memory and displays the pseudocolored result in real-time. In some embodiments, a monitor update frequency of 25 Hz has been achieved with resolutions up to 1400×1024 pixels. In some embodiments, timing for the entire system is provided by an external digital/analog arbitrary waveform generator (National Instruments 6229). In some embodiments, the waveform generator is the "Master Clock" for the system. In some embodiments, once programmed by the host computer, this imaging system of the present disclosure generates all appropriate digital and analog waveforms for controlling the system without further host intervention (for example, FIG. 5).

In some embodiments, a single program controls all aspects of the system including the user interface which is ultimately responsible for guiding the surgeon. In some embodiments, the program is written in C++ using the standard windows API and the latest version of DirectX for best video performance. In some embodiments, the surgeon has direct control over all relevant hardware and software parameters through a common dialog box located on the right side of the screen—this dialog box is visible at all times. In some embodiments, system parameters that can be controlled include: LED intensity, camera gains, camera exposures, acquisition speed, fluorescent image contrast and gamma adjustments, as well as the hue of the pseudocolor display. In some embodiments, system parameters that need to be adjusted often and quickly during a surgical procedure can be controlled with a set of desktop-mounted rotary encoders. In some embodiments, a single video window occupies most of the program's real-estate. In some embodiments, live images of the surgery are displayed in this window.

In some embodiments, additional features of the imaging systems described herein include: 1) a solid state drive for recording of the displayed image sequences in real-time and 2) a method for minimizing distracting specular reflection from wet surfaces in the reflected white light image. In some embodiments, minimization of specular reflection is implemented by using a pair of crossed linear polarizers in the white light optical train, one in front of the white LED and another in front of the color camera (FIG. 7).

In some embodiments the system controller is an Application Specific Integrated Circuit (such as custom Gate Arrays or Field Programmable Gate Arrays) with dedicated memory for implementation of lookup tables (LUT).

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

EXAMPLES

Example 1

The best way to control reflectance and fluorescence independently is to alternate them at 10-60 Hz rather than relying on a set of complex custom interference filters (Gray, D. C. et al. Dual-mode laparoscopic fluorescence image-guided surgery using a single camera. Biomedical optics express Vol. 3 (2012) and Whitney, M. et al. Fluorescent peptides highlight peripheral nerves during surgery in mice. Nature Biotechnology 29: 352-6 (2011)) to generate the final image. Rapid alternation between the reflectance and fluorescent images achieves immediate feedback for the surgeon by combining and displaying these images on a computer monitor in real-time. With this approach, there is no impact on the quality of the white light image and no compromise on the optical design of the fluorescent portion of the optical pathway.

Alternation of the reflectance and fluorescent images is achieved by pulsing each channel's respective light source at high speed. By integrating photons only during each camera's illumination period, complete channel separation is achieved. The resolution and sensor dimensions of the system's cameras are matched to facilitate image registration. Simple image processing provides a continuous high-resolution display with a minimal time lag. The surgeon has little difficulty operating while viewing the monitor rather than looking directly at the surgical field. This time-multiplexing approach allows the spectral characteristics and gains of the reflectance and fluorescence channels to be varied independently and therefore allows maximum flexibility for dealing with different dyes and tissue concentrations during the same imaging session.

In contrast to existing imaging systems there are no restrictions on the type of fluorophores that can be used by the system—all excitation and emission wavelengths are supported. An additional consequence is that multiple fluorophores can be targeted simultaneously, since the entire spectrum from the UV to the infrared is available for fluorophores insuring little overlap in excitation and/or emission spectra.

Additional features of the systems include: 1) a method for minimizing distracting specular reflection from wet surfaces in the reflected white light image. Minimization of specular reflection is implemented by using a pair of crossed linear polarizers in the white light optical train, one in front of the white LED and another in front of the color camera (FIG. 7).

Example 2

Abstract

Although the modern surgical era is highlighted by multiple technological advances and innovations, one area that has remained constant is the dependence of the surgeon's vision on white-light reflectance. This renders different body tissues in a limited palette of various shades of pink and red, thereby limiting the visual contrast available to the operating surgeon. Healthy tissue, anatomic variations, and diseased states are seen as slight discolorations relative to each other and differences are inherently limited in dynamic range. In the upcoming years, surgery will undergo a paradigm shift with the use of targeted fluorescence imaging probes aimed at augmenting the surgical armamentarium by expanding the "visible" spectrum available to surgeons. Such fluorescent "smart probes" will provide real-time, intraoperative, pseudo-color, high-contrast delineation of both normal and pathologic tissues. Fluorescent surgical molecular guidance promises another major leap forward to improve patient safety and clinical outcomes, and to reduce overall healthcare costs. This example provides an overview of current and future surgical applications of fluorescence imaging in diseased and nondiseased tissues and focus on the innovative fields of image processing and instrumentation.

Introduction

In recent years, advances in whole body imaging and diagnostics have enhanced patient selection for surgical interventions. Concomitant innovation in surgical technique and minimally invasive approaches with laparoscopic, endoscopic and robotic techniques has advanced many surgical procedures. In spite of innumerable advances, surgery still relies primarily on white-light reflectance. This approach does not allow differentiation between normal and diseased tissue beyond gross anatomical distortion or discoloration. The emerging field of fluorescent surgical imaging promises to be a powerful enhancement to traditional low-contrast white-light visualization, offering real-time pseudo-color delineation of complex anatomic structures. Improved visualization will lead to more complete removal of disease, decreased inadvertent injury to vital structures, and improved identification for repair of damaged tissues.

Fluorescence imaging for surgical guidance is a rapidly expanding field. A PubMed search for "fluorescence imaging" and "surgery" demonstrates the exponential growth of published efforts; with 36 articles in 1999 rising to over 300 in 2011. The volume of work relating to fluorescence imaging in cancer operations has similarly expanded over the last two decades. Despite this rising excitement, clinical trials have barely begun, (S. G. Piccirillo, S. Dietz, B. Madhu, J. Griffiths, S. J. Price, V. P. Collins, and C. Watts, "Fluorescence-guided surgical sampling of glioblastoma identifies phenotypically distinct tumour-initiating cell populations in the tumour mass and margin," Br. J. Cancer, 107: 462-468, (2012); K. Roessler, A. Becherer, M. Donat, M. Cejna, and I. Zachenhofer, "Intraoperative tissue fluorescence using 5-aminolevolinic acid (5-ALA) is more sensitive than contrast MRI or amino acid positron emission tomography ((18)F-FET PET) in glioblastoma surgery," Neurolog. Res., 34: 314-317, (2012); W. Stummer, A. Novotny, H. Stepp, C. Goetz, K. Bise, and H. J. Reulen, "Fluorescence-guided resection of glioblastoma multiforme by using 5-aminolevulinic acid-induced porphyrins: A prospective study in 52 consecutive patients," J. Neurosurg., 93: 1003-1013, (2000); W. Stummer, U. Pichlmeier, T. Meinel, O. D. Wiestler, F. Zanella, and H. J. Reulen, "Fluorescence-guided surgery with 5-aminolevulinic acid for resection of malignant glioma: A randomised controlled multicentre phase III trial," Lancet Oncology, 7: 392-401, (2006); G. M. van Dam, G. Themelis, L. M. Crane, N. J. Harlaar, R. G. Pleijhuis, W. Kelder, A. Sarantopoulos, J. S. de Jong, H. J. Arts, A. G. van der Zee, J. Bart, P. S. Low, and V. Ntziachristos, "Intraoperative tumor-specific fluorescence imaging in ovarian cancer by folate receptor-alpha targeting: First in-human results," Nature Med., 17: 1315-1319, (2011)) and much more translational effort will be required to harness this exciting technology. The complexity of fluorescent surgical molecular guidance necessitates a multidisciplinary approach as it progresses through development, testing, implementation, and widespread adoption. The future of fluorescence guided surgery depends on the parallel development of high-quality fluorescent compounds that perform specific identification roles, and on image processing and instrumentation to display the images.

A complete list of currently available fluorescent probes is discussed in numerous publications (see, for example, Q. Nguyen and R. Y. Tsien, "Surgical Molecular Navigation with Fluorescence-A New Cutting Edge," Nature Reviews Cancer, 13: 653-62 (2013); S. Luo, E. Zhang, Y. Su, T. Cheng, and C. Shi, "A review of NIR dyes in cancer targeting and imaging," Biomaterials, 32: 7127-7138, (2011)). Discussions of probe biomechanics, and specific applications have also been reported recently. (Q. Nguyen and R. Y. Tsien, "Surgical Molecular Navigation with Fluorescence-A New Cutting Edge," Nature Reviews Cancer, 13: 653-62 (2013); S. L. Troyan, V. Kianzad, S. L. Gibbs-Strauss, S. Gioux, A. Matsui, R. Oketokoun, L. Ngo, A. Khamene, F. Azar, and J. V. Frangioni, "The FLARE intraoperative near-infrared fluorescence imaging system: A first-in-human clinical trial in breast cancer sentinel lymph node mapping," Ann. Surg. Oncology, 16: 2943-2952, (2009); M. C. Pierce, D. J. Javier, and R. Richards-Kortum, "Optical contrast agents and imaging systems for detection and diagnosis of cancer," Int. J. Cancer, 123: 1979-1990, (2008); G. Themelis, J. S. Yoo, K. S. Soh, R. Schulz, and V. Ntziachristos, "Real-time intraoperative fluorescence imaging system using light-absorption correction," J. Biomed. Opt., 14: 064012-064012, (2009); S. Gioux, H. S. Choi, and J. V. Frangioni, "Image-guided surgery using invisible near-infrared light: Fundamentals of clinical translation," Molec. Imag., 9: 237-255, (2010); S. Keereweer, J. D. Kerrebijn, P. B. van Oriel, B. Xie, E. L. Kaijzel, T. J. Snoeks, I. Que, M. Hutteman, J. R. van der Vorst, J. S. Mieog, A. L. Vahrmeijer, C. J. van de Velde, R. J. Baatenburg de Jong, and C. W. Lowik, "Optical image-guided surgery—Where do we stand?," Molec. Imag. Bioi., 13: 199-207, (2011); Y. Liu, A. Q. Bauer, W. J. Akers, G. Sudlow, K. Liang, D. Shen, M. Y. Berezin, J. P. Culver, and S. Achilefu, "Hands-free, wireless goggles for near-infrared fluorescence and real-time image-guided surgery," Surgery, 149: 689-698, (2011); A. Taruttis and V. Ntziachristos, "Translational optical imaging," Amer. J. Roentgenol., 199: 263-271, (2012); N. S. van den Berg, F. W. van Leeuwen, and H. G. van der Poel, "Fluorescence guidance in urologic surgery," Current Opin. Urology, 22: 109-120, (2012); IEEE Reviews In Biomedical Engineering, 6: 178-187, (2013); and F. P. Verbeek, J. R. van der Vorst, B. E. Schaafsma, M. Hutteman, B. A. Bonsing, F. W. van Leeuwen, J. V. Frangioni, C. J. van de Velde, R. J. Swijnenburg, and A. L. Vahrmeijer, "Image-guided hepatopancreatobiliary surgery using near-infrared fluorescent light," J. Hepato-Biliary-Pancreatic Sci., 626-637, (2012)).

The technical challenges of fluorescent probe development, image processing and instrumentation are immense. Creative ingenuity is required to realize the full potential of fluorescence guided surgery. This example offers a framework for conceptualizing fluorescence guided surgery by highlighting current and future surgical applications in diseased and nondiseased tissues. This example focuses on the innovative fields of image processing and instrumentation, which strive to merge the traditional surgical visual field with fluorescent guidance. The discussion on these technologies will focus on fluorescent signal detection, signal-to-noise optimization, and display.

II. VISUALIZATION OF DISEASED AND NONDISEASED TISSUES-A CRITICAL PROBLEM

Surgical management of disease is an integral part of health care. The core goals of surgery are to repair, remove, or correct diseased tissues while limiting un-necessary damage to healthy structures. Achieving these goals allows optimal disease treatment while preserving form and physiological function. Successful surgery depends on multiple factors, first and foremost being visualization. Bringing targeted fluorescence imaging and into the operating room dramatically expands surgeons' visual capabilities, allowing them to see structures as they extend beyond the surface tissue; even prior to their actual physical exposure. Improved visualization with fluorescence labeling enables more complete resection of surgical disease, while protecting adjacent vital structures.

Figure 8:
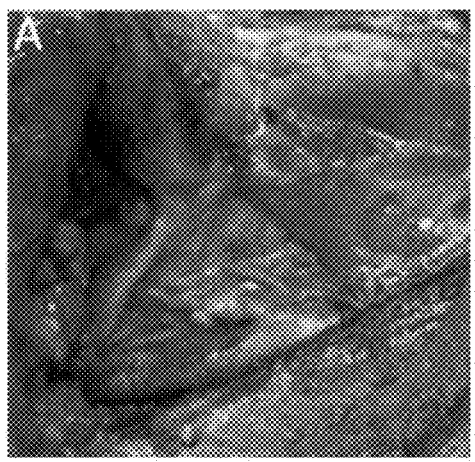
FIG. 8 provides images of nerves, vessels and muscles are not easily differentiated from one another with white light reflectance imaging. Intraoperative view of a lymph node dissection in a patient's neck, showing that large blood vessels and nerve structures are difficult to differentiate from surrounding muscle with white-light reflectance alone (A). The carotid artery (red), jugular vein (blue) and vagus nerve (yellow) arc highlighted in the schematic (B). The vagus nerve is a few millimeters across and represents the largest scale nerve that surgeons identify. The smallest nerves that surgeons must identify are less than a millimeter in diameter.
Figure 8:
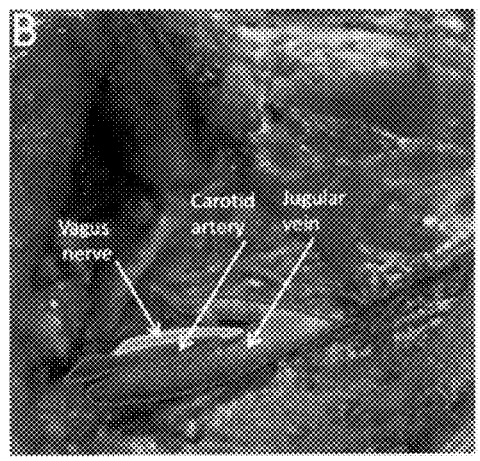

Enhancing the visualization of tissues based on structure could be equated to "painting" tissues in the surgical field to look more like a multicolored anatomy textbook; where nerves are yellow, lymphatics green, veins blue, and arteries red (FIG. 8).

Figure 9:
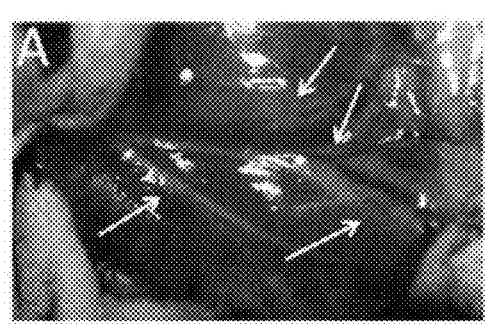
FIG. 9 provides images of fine nerve structures can be obscured by overlying tissue. White light reflectance image showing a facial nerve in a mouse nerve (A). Much greater detail regarding nerve location and branching even under overlying non-nerve structures (compare arrows between A and B) is seen in the fluorescence image following systemic injection of a nerve labeling marker (NP41) (B).
Figure 9:
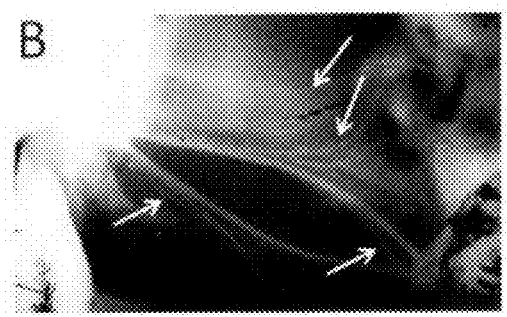

In the images of a mouse facial nerve shown in FIG. 9, a case of normal (nondiseased) facial nerve that is difficult to distinguish with white-light alone is seen. Viewing this same surgical field using fluorescence guidance allows easy identification of the delicate tendrils of facial nerve as they course near and around structures which otherwise obscure the view (M. Whitney, J. Crisp, L. Nguyen, B. Friedman, L. Gross, P. Steinbach, R. Tsien, and Q. Nguyen, "Fluorescent peptides highlight peripheral nerves during surgery in mice," Nature Biotechnol., 29: 352-356, (2011)). Protecting fine nerves during surgery requires high-contrast visualization. Unintentional damage to these fine nerves means postoperative functional deficits or pain.

Figure 10:
FIG. 10 provides cancer margins are not easily discernible with white light inspection. Color photograph showing a patient with a tongue cancer. The surface of the tumor is seen as a whitish growth, with a red-pink background of tongue mucosa (A). Beneath the surface, cancer growth extends in an unpredictable pattern (B: schematic, green line). The green line represents deep tumor growth. In order to achieve complete resection, the surgeon must estimate the tumor extent when making cuts around the cancer (B: schematic, blue line). Depending on the actual tumor spread, the cut edges can be variably close to cancer cells, and there is a risk of having a positive margin.
Figure 10:
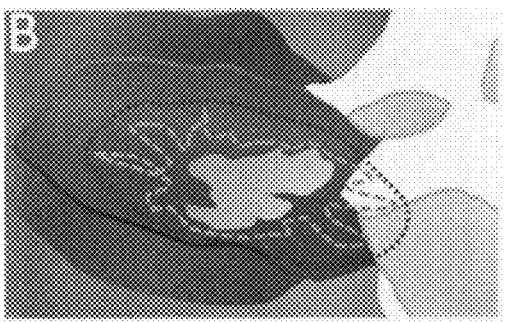

An example where unpredictable tumor growth leads to more aggressive surgical resection is shown in FIG. 10. A squamous cell cancer is readily seen as gross structural distortion and discoloration on the side of the tongue. Successful surgical removal of this cancer depends on knowing the extent of the tumor cells. Beneath the surface where the cancer extends in an unpredictable growth pattern (FIG. 3, green line), visual contrast no longer allows the surgeon to reliably see the tumor. Knowing the risk of leaving cancer cells behind, the surgeon makes an educated guess regarding the extent of cancer growth and makes cuts accordingly (FIG. 10, blue line). The cut edges of the surgical specimen are checked with intraoperative pathological review which adds to operative time and cost. Still sometimes, the final pathology shows the undesirable finding of cancer cells at the edge of the cancer resection; a "positive margin."

Figure 11:
FIG. 11 provides fluorescent labeling of tumor aids removal. In a mouse model of cancer, no residual tumor on the sciatic nerve is apparent to the human eye using white light reflectance (A). (B) With fluorescence imaging following injection of a molecularly targeted probe (activatable cell penetrating peptide, ACPP), it is clear that there is residual cancer tissue (arrow). (C) Pseudocolor overlay of the fluorescence image on top of the white light reflectance image shows the surgical view that retains anatomical details of standard surgery while adding the molecular details of the fluorescently labeled probe.
Figure 11:
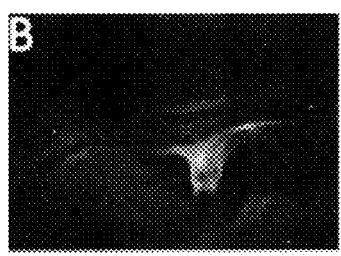
Figure 11:

An example where tumor cells can be invisible to the human eye, but readily seen with targeted fluorescence imaging can be seen in FIG. 11. Fluorescent activatable cell-penetrating peptide (ACPP) was used in a mouse model of metastatic breast cancer (Q. T. Nguyen, E. S. Olson, T. A. Aguilera, T. Jiang, M. Scadeng, L. G. Ellies, and R. Y. Tsien, "Surgery with molecular fluorescence imaging using activatable cell-penetrating peptides decreases residual cancer and improves survival," Proc. Nat. Acad. Sci. USA, 107: 4317-4322, (2010)). Cancer cells that could have easily been left behind after surgery stand out in the fluorescence image. Fluorescent labeling of malignant cells would remove potential ambiguity of the cancer borders during surgical dissection where most tissues are varying shades of reds and pink, leading to more effective and safer surgery.

III. FLUORESCENT "VISUAL ENHANCERS" AND "SMART PROBES" FOR SURGERY

Surgical fluorescence imaging is already being implemented through the use of indocyanine green (ICG) and fluoresce in. These dyes are nontargeted fluorescent "visual enhancers" that can be used to highlight blood vessels, ducts, and other structures. Despite their nontargeted labeling, they have significant utility in many surgical applications. and ICG, "smart probes" are fluorescently labeled agents targeted to a specific tissue type or biochemical process. This affords the possibility of true surgical molecular guidance. Targeted smart probes can work via adherence to tissue specific markers such as antibody recognition of cell surface antigens, (S. Kaushal, M. K. McElroy, G. A. Luiken, M. A. Talamini, A. R. Moossa, R. M. Hoffman, and M. Bouvet, "Fluorophore-conjugated anti-CEA antibody for the intraoperative imaging of pancreatic and colorectal cancer," J. Gastroint. Surg., 12: 1938-1950, (2008); H. S. Tran Cao, S. Kaushal, C. A. Metildi, R. S. Menen, C. Lee, C. S. Snyder, K. Messer, M. Pu, G. A. Luiken, M. A. Talamini, R. M. Hoffman, and M. Bouvet, "Tumor-specific fluorescence antibody imaging enables accurate staging laparoscopy in an orthotopic model of pancreatic cancer," Hepato-Gastroenterology, 59: 1994-1999, (2012)) peptide or aptamers with increased affinity for cell surface proteins (M. Whitney, J. Crisp, L. Nguyen, B. Friedman, L. Gross, P. Steinbach, R. Tsien, and Q. Nguyen, "Fluorescent peptides highlight peripheral nerves during surgery in mice," Nature Biotechnol., 29: 352-356, (2011); A. P. Wu, M. A. Whitney, J. L. Crisp, B. Friedman, R. Y. Tsien, and Q. T. Nguyen, "Improved facial nerve identification with novel fluorescently labeled probe," Laryngoscope, 121: 805-810, (2011)) or through specific enzymatic localization and amplification (Q. T. Nguyen, E. S. Olson, T. A. Aguilera, T. Jiang, M. Scadeng, L. G. Ellies, and R. Y. Tsien, "Surgery with molecular fluorescence imaging using activatable cell-penetrating peptides decreases residual cancer and improves survival," Proc. Nat. Acad. Sci. USA, 107: 4317-4322, (2010); E. S. Olson, M. A. Whitney, B. Friedman, T. A. Aguilera, J. L. Crisp, F. M. Baik, T. Jiang, S. M. Baird, S.

Tsimikas, R. Y. Tsien, and Q. T. Nguyen, "In vivo fluorescence imaging of atherosclerotic plaques with activatable cell-penetrating peptides targeting thrombin activity," Integrative Biol., 4: 595-605, (2012); X. Shu, V. Lev-Ram, E. S. Olson, T. A. Aguilera, T. Jiang, M. Whitney, J. L. Crisp, P. Steinbach, T. Deerinck, M. H. Ellisman, L. G. Ellies, Q. T. Nguyen, and R. Y. Tsien, "Spiers Memorial Lecture. Breeding and building molecular spies," Faraday Discuss., 149: 9-9, (2011); E. S. Olson, T. Jiang, T. A. Aguilera, Q. T. Nguyen, L. G. Ellies, M. Scadeng, and R. Y. Tsien, "Activatable cell penetrating peptides linked to nanoparticles as dual probes for in vivo fluorescence and MR imaging of proteases," Proc. Nat. Acad. Sci. USA, 107: 4311-4316, (2010); E. S. Olson, T. A. Aguilera, T. Jiang, L. G. Ellies, Q. T. Nguyen, E. H. Wong, L. A. Gross, and R. Y. Tsien, "In vivo characterization of activatable cell penetrating peptides for targeting protease activity in cancer," Integrative Biol., 1: 382-393, (2009); T. Jiang, E. S. Olson, Q. T. Nguyen, M. Roy, P. A. Jennings, and R. Y. Tsien, "Tumor imaging by means of proteolytic activation of cell-penetrating peptides," Proc. Nat. A cad. Sci. USA, 101: 17867-17872, (2004); E. Deu, M. Verdoes, and M. Bogyo, "New approaches for dissecting protease functions to improve probe development and drug discovery," Nature Struct. Molec. Bioi., 19: 9-16, (2012); G. Blum, R. M. Weimer, L. E. Edgington, W. Adams, and M. Bogyo, "Comparative assessment of substrates and activity based probes as tools for non-invasive optical imaging of cysteine protease activity," PLoS One, 4: e6374-e6374, (2009); G. Blum, G. von Degenfe ld, M. J. Merchant, H. M. Blau, and M. Bogyo, "Noninvasive optical imaging of cysteine protease activity using fluorescently quenched activity-based probes," Nature Chem. Biol., 3: 668-677, (2007); G. Blum, S. R. Mullins, K. Keren, M. Fonovic, C. Jedeszko, M. J. Rice, B. F. Sloane, and M. Bogyo, "Dynamic imaging of protease activity with fluorescently quenched activity-based probes," Nature Chem. Bioi., 1: 203-209, (2005); D. Kato, K. M. Boatright, A. B. Berger, T. Nazif, G. Blum, C. Ryan, K. A. Chehade, G. S. Salvesen, and M. Bogyo, "Activity-based probes that target diverse cysteine protease families," Nature Chem. Bioi., 1: 33-38, (2005); R. A. Sheth, R. Upadhyay, L. Stangenberg, R. Sheth, R. Weissleder, and U. Mahmood, "Improved detection of ovarian cancer metastases by intraoperative quantitative fluorescence protease imaging in a pre-clinical model," Gynecologic Oncol., 112: 616-622, (2009); J. L. Figueiredo, H. Alencar, R. Weissleder, and U. Mahmood, "Near infrared thoracoscopy of tumoral protease activity for improved detection of peripheral lung cancer," Int. J. Cancer, 118: 2672-2677, (2006); K. E. Bullok, D. Maxwell, A. H. Kesarwala, S. Gammon, J. L. Prior, M. Snow, S. Stanley, and D. Piwnica-Worms, "Biochemical and in vivo characterization of a small, membrane-permeant, caspase-activatable far-red fluorescent peptide for imaging apoptosis," Biochem., 46: 4055-4065, (2007)). Both traditional fluorescent visual enhancers and fluorescently labeled-smart probes increase the contrast across key tissue types to augment the surgeon's visualization over traditional white-light reflectance modalities.

IV. CLINICAL NEED AND APPLICATIONS

A. Non Diseased Tissues/Structural Targets

In any surgical procedure, accurate identification and preservation of normal structures is critical to avoid iatrogenic injury. Most fluorescent agents that highlight nondiseased tissues take advantage of structural characteristics or prevalent binding sites, and illuminate an entire structure or tissue-type. Probes highlighting nondiseased tissues would benefit trauma and reconstructive procedures, as well as any case where improved identification of vital structures would make surgery safer or more efficient.

Following trauma, the repair of injured bones, tissues, nerves, and vessels requires accurate identification of relevant structures in the context of distorted anatomy. Frequently, nerves and tissues encountered in the surgical dissection are not easily identified because of tissue edema, inflammatory changes, and/or scarring. In the case of traumatic motor nerve transection, the distal nerve-end may be identified with electromyography for a several days following injury. Unfortunately, this technique is not useful at later times, it cannot help identify the proximal nerve-end, and it is not useful for autonomic and sensory nerves. This is just one realm where fluorescent targeting of nerve tissue would powerfully augment traditional identification techniques. The identification of healthy nerves can be expanded to a myriad of surgeries where fine nerve anatomy portends increased risks for damage and visualizing and these structures can decrease morbidity. An overview of this and other structural applications for surgical fluorescent imaging is provided in Table 7.

Table 7 describes non-diseased tissues (structural targets) fluorescent visual enhancers commonly work through non-specific structural labeling in non-diseased tissues. Several categories of structural targets are provided corresponding to current and future surgical applications. Complications that these fluorescent enhancers could decrease or help surgeons avoid are also provided.

TABLE 7

| Structural Applications | Possible Targets | Related Complications |
|---|---|---|
| Nerve | Nerve identification, neurorrhaphy, complex otologic procedures, nerve release, minimally | Prolonged time to nerve identification Iatrogenic damage |
| Ureter | Improved identification in minimally invasive urologic, gynecologic, and colorectal procedures | Iatrogenic injury |
| Blood Vessel | Evaluate vascular anatomy, assess graft patency and perfusion, evaluate vascular lesions Cardiac surgery Vascular surgery | Sub-optimal vessel reconstruction Oversight of lumen stenosis Thromboembolic events |

TABLE 7-continued

| Structural Possible Applications | Targets | Related Complications |
|---|---|---|
| Lymphatic & Lymph Node | Lymph node/metastasis mapping Sentinel lymph node biopsy identification of lymphatic channels Chyle leak repair | Incomplete removal of at-risk lymphatic structures Inaccurate or incomplete sentinel node sampling Damage to lymphatic structures with resultant leak or lymphedema |
| Bile & Pancreatic Duct | Liver mapping and cholangiography Cholecystectomy and pancreaticoduodenectomy Organ transplantation Endoscopic procedures | Bile duct injury Suboptimal anastamoses Improper resection planning Prolonged time to identification of structures |
| Cerebrospinal Fluid (CSF) | CSF leak identification and repair Complex neuro- and neurotologicsurgeries | Iatrogenic CSF leak Failure to find and effectively treat CSF leak |

B. Diseased Tissues/Functional Targets

Diseased tissues offer unique opportunities for targeted molecular guidance using fluorescent smart probes. The broad surgical categories of infection, atherosclerosis, and neoplasms represent three realms of surgery that are well-suited for future fluorescence imaging applications.

i) Infection/Devitalized Tissue:

In cases of infection or tissue ischemia, surgery is often used to excise devitalized tissue. Surgical debridement relies on white-light reflectance to determine which tissue is healthy, and which is nonviable or has vascular compromise. This technique has low sensitivity and specificity and can lead to excessive removal of healthy tissue.

In the setting of acute invasive fungal sinusitis, current management depends on aggressive, thorough debridement of all involved structures. The extent of excision is largely dictated by the gross appearance of tissues-described as subtle hues of grey amidst a sea of pink mucosa. The surgery relies on pathological sections of the surgical borders to assess the extent of fungal invasion. If fungal spread could be more sensitively detected in the operating room, surgery could spare adjacent un-involved structures and be more efficient. Targeted fluorescent probes could fulfill this need by illuminating necrotic tissue, or even fungal species themselves.

With a similar goal, fluorescein has been used in general surgery for some time to identify devitalized segments of intestine, but there is certainly room for improvement. Better visualization of infected, devitalized, and ischemic tissue would benefit surgeons of all specialties.

ii) Atherosclerosis:

In addition to cancer, atherosclerosis is a major cause of morbidity and death worldwide (V. L. Roger, et al., "Executive Summary: Heart Disease and Stroke Statistics-2012 Update: A Report From the American Heart Association," Circulation, 125: 188-197, (2012)). The disruption of plaques during surgical treatment of atherosclerosis such as in carotid endarterectomy (removal of atherosclerotic plaques from the carotid arteries) and coronary artery bypass grafting (surgically adding another vessel to provide blood flow to different parts of the heart when the native artery is blocked), can cause an embolic stroke or a heart attack, respectively. While taking into account associated clinical factors, candidacy for these two procedures is largely anatomic in nature; dependent on the location and degree of vessel stenosis (L. D. Hillis, et al., "2011 ACCF/AHA guideline for coronary artery bypass graft surgery: Executive summary: A report of the American College of Cardiology Foundation/American Heart Association Task Force on Practice Guidelines," J. Thoracic Cardiovasc. Surgery, 143: 4-34, (2012); J. J. Ricotta, A. Aburahma, E. Ascher, M. Eskandari, P. Faries, and B. K. La I, "Updated Society for Vascular Surgery guidelines for management of extracranial carotid disease: Executive summary," J. Vascular Surgery, 54: 832-836, (2011)). Plaque specific factors such as likelihood of rupture are not easily pre-Failure to find and effectively treat CSF leak dieted using current methods and are usually not part of the presurgical decision making process. Importantly, the majority of acute heart attack and stroke occur not as a gradual progression of increasing stenosis, but rather as a sudden event where the blood flow through a diseased vessel is abruptly disrupted from an acute embolic event. Thus, accurate identification of these "vulnerable" plaques in susceptible patients would mitigate unnecessary surgery in patients with stable plaques and identify patients at high risk of plaque rupture (H. Ouldzein, M. Elbaz, J. Roncall i, R. Cagnac, D. Carrie, J. Puel, and M. J. Alibelli-Chemarin, "Plaque rupture and morphological characteristics of the culprit les ion in acute coronary syndromes without significant angiographic lesion: Analysis by intravascular ultrasound," Ann. Cardiologie D'angeiologie, 61: 20-26, (2012); Z. Wu, C. Yang, and D. Tang, "In vivo serial MRI-based models and statistical methods to quantify sensitivity and specificity of mechanical predictors for carotid plaque rupture: Location and beyond," J. Biomech. Eng., 133: 064503-064503, (2011); E. M. Ruiz, T. G. Papaioannou, M. Vavuranakis, C. Stefanadis, M. Naghavi, and I. A. Kakadiaris, "Analysis of contrast-enhanced intravascular ultrasound images for the assessment of coronary plaque neoangiogenesis: Another step c loser to the identification of the vulnerable plaque," Current Pharm. Des., 18: 2207-2213, (2012); S. P. Jackson, "Arterial thrombosis—Insidious, unpredictable and deadly," NatureMed., 17: 1423-1436, (2011)). Furthermore, the ability to observe processes leading to vulnerable plaque formation can be applied to other noninvasive imaging modalities (CT, MRI, and ultrasound) (Y. Ozaki, A. Tanaka, T. Tanimoto, H. Kitabata, M. Kashiwagi, T. Kubo, S. Takarada, K. Ishibashi, K. Komukai, Y. Ino, K. Hirata, M. Mizukoshi, T. lmanishi, and T. Akasaka, "Thin-cap fibroatheroma as high-risk plaque for microvascular obstruction in patients with acute coronary syndrome," Circulation. Cardiovasc. Imag., 4: 620-627, (2011); M. Kashiwagi, A. Tanaka, H. Kitabata, H. Tsujioka, H. Kataiwa, K. Komukai, T. Tanimoto, K. Takemoto, S. Takarada, T. Kubo, K. Hirata, N. Nakamura, M. Mizukoshi, T. Imanishi, and T. Akasaka, "Feasibility of noninvasive assessment of thin-cap fibroatheroma by multidetector computed tomography," JACC Cardiovasc. Imag., 2: 1412-1419, (2009); G. C. Makris, A. N. Nicola ides, X. Y. Xu, and G. Geroulakos, "Introduction to the biomechanics of carotid plaque pathogenesis and rupture: Review of the clinical evidence," Br. J. Radiol., 83: 729-735, (2010); S. Partovi, M. Loebe, M. Aschwanden, T. Baldi, K. A. Jager, S. B. Feinstein, and D. Staub, "Contrast-enhanced ultrasound for assessing carotid atherosclerotic plaque lesions," Amer. J. Roentgenol., 198: W13-9, (2012)).

iii) Cancer:

With the primary treatment modality for most solid cancer being surgery, [47] complete removal of all malignant cells is unquestionably essential. If all cancer cells are removed with surgery, the patient is cured of that cancer. Unfortunately, visual inspection using white-light reflectance has very low sensitivity for identifying malignant cells. This leads to a considerable amount of "educated guess-work" when it comes to the extent of tissue removal for a cancer surgery (see FIG. 10). Molecularly targeted fluorescent probes would allow improved visualization of tumor extent and detection of cancer cells that may have otherwise been left in the patient if relying on white-light reflectance alone. The removal of lymph nodes that potentially harbor tumor cells (sentinel or regional lymph node dissection) is another frequently performed cancer surgery that would benefit from the fluorescent illumination of cancer cells. In the context of cancer surgery, the ability to accurately visualize tumor cells at the molecular level at both primary and metastatic sites will improve diagnostic accuracy, reduce unnecessary surgery, and improve completeness of resection. Details regarding specific probes can be found in a recent review (see, Q. Nguyen and R. Y. Tsien, "Surgical Molecular Navigation with Fluorescence-A New Cutting Edge," Nature Reviews Cancer 13: 653-62, (2013)) and recent work in fluorescence guidance in diseased surgical processes is summarized in Table 8.

Table 8 describes diseased tissues diseased tissues offer unique opportunities for surgeons to apply specific, targeted fluorescent smart probes. Functional targets, recent work in various applications, and possible complications are summarized.

tation of fluorescent guided surgery in humans will require advances in signal detection, signal-to-noise optimization, and display.

A. Detection

White-light reflectance is inherently brighter than fluorescence, in that the fraction of incident photons returned by reflectance is much higher than that from fluorescence, even from a strongly labeled tissue. Also, fluorescence requires spectral separation between intense short-wavelength excitation and relatively dim longer-wavelength emission, filtered to remove reflected excitation wavelengths. The simplest but least flexible solution, feasible mainly for dyes excited in the violet or blue range, is to tailor excitation and emission filters to provide a mixture of reflectance and fluorescence directly visible by eye or a standard color camera. An early example was the visualization of the fluorescence (Leica FL400-excitation at 380-420 nm, display at 480-720 nm and Zeiss OPMI Pentero-excitation 400-410 nm, display 620-710 nm) from protoporphyrin IX generated in tumors by systemic administration of the metabolic precursor, 5-aminolevulinic acid (W. Stummer, U. Pichlmeier, T. Meinel, O. D. Wiestler, F. Zanella, and H. J. Reulen, "Fluorescence-guided surgery with 5-aminolevulinic acid for resection of malignant glioma: A randomised controlled multicentre phase Ill trial," Lancet Oncology, 7: 392-401, (2006)). The red emission filter was deliberately made slightly leaky to violet so that normal tissue landmarks and surgical instruments were visible by violet reflectance while cancer tissue glowed red. Normal full color reflectance was sacrificed so that image processing could be completely avoided. Similarly, fluorescein fluorescence (excitation 488 nm, emission >500 run) can be viewed with an excitation filter mainly passing blue but with some leakage of green and red, paired with an emission filter Incomplete lymph node removal preferentially passing green but with slight leakage of blue and somewhat more of red. The leakages allow blue, green, and red reflectances to generate a white-light reflectance image with green fluorescence superimposed (Zeiss Pentero). The advantage of these approaches is that the only modification of standard equipment is the

TABLE 8

| Functional Applications Related Complications | Targets | Devitalized, Surgical debridement [102] and Suboptimal identification of |
|---|---|---|
| Devitalized, Inflamed, & Infected Tissue | Surgical debridement and detection of wound contamination Inflammatory detection Vascular/microvascular surgery Tissue anastomosis | Suboptimal identification of devitalized tissue with resultant overly-aggressive surgery Anastomotic failure |
| Atherosclerosis | Plaque identification and therapeutic interventions | Disruption or misidentification of plaques |
| Cancer & Neoplasm | Mucosal neoplasm Solid organ tumor-margin detection | Incomplete cancer removal (positive margins) Incomplete lymph node removal |

V. INSTRUMENTATION

It is often not practical to conduct surgery while viewing only the fluorescence of the contrast agent. Instead, fluorescence images should be superimposed continuously in real time and in precise spatial register with reflectance images showing the morphology of the normal tissue and the location of the surgical instruments. Large-scale implementation of judiciously tailored excitation and emission filters. The disadvantages are 1) inflexibility, in that the filters have to be optimized for a given tissue concentration of a given dye, 2) spectral distortion of the reflectance image (in the worst case, confinement to violet), and 3) complete reliance on the surgeon's subjective color discrimination to decide how much fluorescence is sufficient to warrant resection.

The next higher level of sophistication is to provide separate cameras for reflectance and fluorescence respectively, so that the gain of each can be separately controlled, and the reflectance camera does not have to look through the emission filter required by the fluorescence camera. This is the obvious approach when the fluorophore excitation and emission wavelengths are in the NIR, (S. L. Troyan, V. Kianzad, S. L. Gibbs-Strauss, S. Gioux, A. Matsui, R. Oketokoun, L. Ngo, A. Khamene, F. Azar, and J. V. Frangioni, "The FLARE intraoperative near-infrared fluorescence imaging system: A first-in-human clinical trial in breast cancer sentinel lymph node mapping," Ann. Surg. Oncology, 16: 2943-2952, (2009); A. M. De Grand and J. V. Frangioni, "An operational near-infrared fluorescence imaging system prototype for large animal surgery," Technol. Cancer Res. Treatment, 2: 553-562, (2003)) because the surgical field can be illuminated with white visible light (400-650 nm) plus 760 nm in the case of indocyanine green. The reflectance camera sees the white-light reflectance but not the NIR, while the fluorescence camera sees the 800 nm emission through a suitable long-pass filter, so that the reflectance and fluorescence channels are independently adjustable in gain (S. L. Troyan, V. Kianzad, S. L. Gibbs-Strauss, S. Gioux, A. Matsui, R. Oketokoun, L. Ngo, A. Khamene, F. Azar, and J. V. Frangioni, "The FLARE intraoperative near-infrared fluorescence imaging system: A first-in-human clinical trial in breast cancer sentinel lymph node mapping," Ann. Surg. Oncology, 16: 2943-2952, (2009)). A bit more ingenuity is required when the fluorophore excitation and emission are at visible wavelengths. One solution is to confine the excitation to three narrow spectral lines of blue, green, and red, say 488, 543, and 633 nm (G. Themelis, J. S. Yoo, and V. Ntziachristos, "Multispectral imaging using multiple-bandpass filters," Opl. Leu., 33: 1023-1025, (2008)) whose relative intensities are adjusted to generate a reasonable simulation of white-light for the reflectance camera to monitor. Ideally, one of these wavelengths should be optimal for exciting the fluorophore. Meanwhile the fluorescence camera looks through an emission filter selective for one or more of the wavelength gaps between the sharp excitation lines. Depending on the fluorophore, some sacrifice of emission band-pass is likely to be necessary to avoid interference from the next longer illumination line. Also, it is cumbersome to adjust the intensity of the fluorescence excitation relative to the other lines making up the white-light illumination. In our view, the best way to control reflectance and fluorescence independently is to alternate them at 15-25 Hz rather than rely on complex custom interference filters (M. Whitney, J. Crisp, L. Nguyen, B. Friedman, L. Gross, P. Steinbach, R. Tsien, and Q. Nguyen, "Fluorescent peptides highlight peripheral nerves during surgery in mice," Nature Biotechnol., 29: 352-356, (2011); D. C. Gray, E. M. Kim, V. E. Cotero, A. Bajaj, V. P. Staudinger, C. A. Tan Hehir, and S. Yazdanfar, "Dual-mode laparoscopic fluorescence image-guided surgery using a single camera," Biomed. Opt. Exp., 3:1880-1890, (2012)). Light-emitting diodes are readily pulsed to provide 20-33 ms white-light followed by 20-33 ms fluorescence excitation. Light returning from the surgical field is split by a 90:10 neutral beam-splitter to monochrome fluorescence and color reflectance cameras, each of which integrates photons during its appropriate illumination period. The resolutions and sensor dimensions of the two cameras are matched to facilitate registration of their images. Simple image processing provides a continuous high-resolution display with an imperceptible lag time. Provided that the display is fast enough and has enough resolution, there is no difficulty operating while viewing the monitor rather than looking directly at the actual surgical field. This time-multiplexing approach allows the spectral characteristics and gains of the reflectance and fluorescence channels to be varied completely independently and therefore allows maximum flexibility to cope with different dyes and tissue concentrations during the same imaging session in the same patient. Insertion of polarizers into the white-light and reflectance channels to attenuate distracting specular reflections from shiny wet surfaces can also be useful.

Fluorescence guided surgery is important across both "open" and "minimally invasive" procedures. The basic concepts of signal detection are the same for both applications. Wide-field detection comprises a camera directed into an open surgical field, as the surgeon operates with direct line-of-sight visualization. The resultant fluorescence image is displayed on a screen for the surgeon to refer to in real-time during the operation. Minimally invasive surgeries are performed with endoscopes, and the surgeon does not have direct line-of-sight into the surgical field. For minimally invasive applications, detection instrumentation must be miniaturized to adapt to the endoscopic setup. Signal strength decreases with the use of smaller and smaller endoscopes, requiring improved detection and signal optimization techniques.

C. Display

For the user interface display, the simple approach is to show the reflectance and fluorescence images side-by-side or alternating on a single monitor. This can impose an unnecessary strain on the surgeon to mentally register the two images accurately. A better solution is to display the fluorescence in a pseudo-color such as green or aqua, normally never present in tissue, superimposed on the color reflectance image (A. M. De Grand and J. V. Frangioni, "An operational near-infrared fluorescence imaging system prototype for large animal surgery," Technol. Cancer Res. Treatment, 2: 553-562, (2003)). Simply averaging the reflectance and fluorescence pseudo-color images makes both look dim. The fluorescence intensity F as a transparency factor where the (displayed intensity) R,G,B=(1−F/max) (reflectance intensity)R,G,B+(F/Fmax) (saturated pseudo-color)R,G,B is used herein. Here max is the maximum allowed value of F, either auto-scaled from the actual image or preset by the user. There are times during the operation when the surgeon prefers to see just the standard reflectance image or the fluorescence image alone, a foot pedal for hands-free cycling between these two modes and the overlay mode is provided.

A logical further extension is to provide a second fluorescence channel at another emission wavelength. One obvious purpose would be to visualize both diseased tissue to be resected (e.g., tumor) and normal tissue to be spared (e.g., nerve) effectively simultaneously, using two targeted agents operating at well-separated wavelengths (M. Whitney, J. Crisp, L. Nguyen, B. Friedman, L. Gross, P. Steinbach, R. Tsien, and Q. Nguyen, "Fluorescent peptides highlight peripheral nerves during surgery in mice," Nature Biotechnol., 29: 352-356, (2011)). Another application is to image probes whose emission spectrum shifts from one wavelength band to another upon biochemical activation. The most common mechanism for such probes is that they contain two fluorophores interacting by fluorescence resonance energy transfer (FRET), which quenches the shorter-wavelength donor dye while sensitizing its longer-wavelength acceptor partner. Cleavage of the linker between the probes disrupts FRET so that the emission spectrum reverts to that of the donor alone. Displaying a ratio of the two emission bands isolates the degree of cleavage while canceling out many factors such as probe concentration, tissue thickness, excitation intensity, absorbances that affect both wavelengths equally, and motion artifacts. Emission ratioing can thus significantly increase the sensitivity and specificity of tumor or atherosclerotic plaque detection, justifying the increased complexity of the probe molecules and instrumentation (M. Whitney, E. N. Savariar, B. Friedman, R. A. Levin, J. L. Crisp, H. L. Glasgow, R. Lefkowitz, S. R. Adams, P. Steinbach, N. Nashi, Q. T. Nguyen, and R. Y. Tsien, "Ratiometric activatable cell penetrating peptides provide rapid in vivo readout of thrombin activation," Angewandte Chemie Intl. Ed., 52: 325-330, (2013); and E. N. Savariar, C. Felsen, N. Nashi, T. Jiang, L. G. Ellies, P. Steinbach, R. Y. Tsien, and Q. T. Nguyen, "Real time in vivo molecular detection of primary tumors and metastases with ratiometric activatable cell penetrating peptides," Cancer Res., 73: 855-64, (2013)).

VI. CONCLUSION

The principles of addressing diseased and abnormal tissues while preserving adjacent structures will forever stand as a central tenet of surgical practice. Minimally invasive surgical techniques have altered the mechanics of many procedures and surgical practice has to evolve along with these emerging technologies. Working through minimally invasive interfaces has sacrificed the tactile feedback of directly working with tissue and forced surgeons to rely even more heavily on tissue visualization. Thus, a medical specialty traditionally dependent on touch becomes more dependent on vision alone. Any real time improvement in the intraoperative visual differentiation between different tissue types would represent a significant advance.

This is an exciting era, because surgical fluorescence imaging promises to be this much-needed advance. Along with these advances, there remain challenges of defining clinical endpoints and identifying which patients/surgeries would most benefit from fluorescent navigation techniques. In addition to the molecular challenges of developing better fluorescent probes, signal detection, signal-to-noise optimization, and display considerations represent the current technologic obstacles to the realization of real-time, intraoperative, pseudo-color, high-contrast fluorescent guided surgery.

The examples set forth above are provided to give those of ordinary skill in the art a complete disclosure and description of how to make and use the embodiments of the compositions, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated herein by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the disclosure is to be limited only by the terms of the appended claims, along with the full scope of equivalents to which the claims are entitled.

What is claimed is:

1. An imaging system for rapid alternation of a white-light reflectance image and at least one fluorescence image for fluorescence guided surgery applications, comprising:
   (A) a light source unit for providing one or more illumination and excitation lights to a target, the light source unit comprising a plurality of light engines, wherein
      (i) a first light engine in the plurality of light engines emits a first light for illuminating the target, and
      (ii) a second light engine in the plurality of light engines emits a second light for exciting a first fluorophore in the target;
   (B) a detection unit comprising a plurality of detectors for detecting reflectance and fluorescence from the target, thereby producing a plurality of images including the white-light reflectance image and the at least one fluorescence image, wherein
      (i) a first detector in the plurality of detectors detects the reflectance from the target, thereby producing the white-light reflectance image, and
      (ii) a second detector in the plurality of detectors detects a first fluorescence emitted by the excited first fluorophore, thereby producing the at least one fluorescence image;
   (C) one or more first optical trains that homogenize and direct the one or more illumination and excitation lights from the light source unit to the target and one or more second optical trains that direct and focus the reflectance and fluorescence from the target to the detection unit, wherein the one or more first optical trains comprises an achromatic lens pair, a light guide, and a light pipe homogenizer, wherein the light pipe homogenizer is positioned between the achromatic lens pair and the light guide; and
   (D) a computer embedded control unit for controlling the light source unit and the detection unit, wherein said control unit controls electronic switching to turn on and off said first light engine and said second light engine.

2. The imaging system of claim 1, wherein each the plurality of light engines comprises at least one high speed light source.

3. The imaging system of claim 2, wherein the high speed light sources are selected from the group consisting of LEDs, lasers, pulsed xenon lamps and any other light source capable of rapid On and Off switching.

4. The imaging system of claim 1, wherein each light engine in the plurality of light engines can be sequentially energized at a frequency above the flicker fusion frequency for human vision.

5. The imaging system of claim 1, wherein the light source unit is controlled by the control unit such that said first light engine and said second light engine are energized sequentially.

6. The imaging system of claim 1, wherein the control unit synchronizes the light source unit and the detection unit.

7. The imaging system of claim 1, wherein the first detector in the plurality of detectors comprises a color camera.

8. The imaging system of claim 1, wherein the second detector in the plurality of detectors comprises a first monochrome camera.

9. The imaging system of claim 1, wherein the light source unit further comprises a third light engine in the plurality of light engines that emits a third light for exciting a second fluorophore in the target, and wherein the detection unit further comprises a third detector in the plurality of detectors that detects a second fluorescence emitted by the excited second fluorophore, thereby producing a second fluorescence image.

10. The imaging system of claim 9, wherein said third detector in the plurality of detectors comprises a monochrome camera.

11. The imaging system of claim 1, wherein said electronic switching to turn on and off of said first light engine and said second light engine is at a switching rate of less than 1 msec.

12. The imaging system of claim 1, wherein said control unit synchronizes said first detector with electronic switching of said first light engine and said second detector with electronic switching of said second light engine.

13. The imaging system of claim 1, further comprising a display unit that displays the plurality of images by overlying the white-light reflectance image with the at least one fluorescence image in real-time.

* * * * *

UNITED STATES PATENT AND TRADEMARK OFFICE
CERTIFICATE OF CORRECTION

PATENT NO. : 10,231,626 B2
APPLICATION NO. : 14/216704
DATED : March 19, 2019
INVENTOR(S) : Paul Steinbach, Quyen T. Nguyen and Roger Y. Tsien Page 1 of 1

It is certified that error appears in the above-identified patent and that said Letters Patent is hereby corrected as shown below:

In the Specification

In Column 1, beginning at Line 16, please amend the paragraph below the STATEMENT AS TO RIGHTS TO INVENTIONS MADE UNDER FEDERALLY-SPONSORED RESEARCH OR DEVELOPMENT from:
This invention was made with Government support under CA158448, EB008122, and EB014929 awarded by the National Institutes of Health and W81XWH-05-I-0183, W81XWH-09-I-0699 awarded by the Army. The Government has certain rights in this invention.

To:
This invention was made with government support under CA158448, EB008122, and EB014929 awarded by the National Institutes of Health, and under W81XWH-05-1-0183 and W81XWH-09-1-0699 awarded by the Defense Health Agency, Medical Research and Development Branch. The government has certain rights in the invention.

Signed and Sealed this
Tenth Day of February, 2026

John A. Squires
*Director of the United States Patent and Trademark Office*